United States Patent
Salhia

(10) Patent No.: US 10,697,021 B2
(45) Date of Patent: Jun. 30, 2020

(54) METHODS OF DETECTING BREAST CANCER BRAIN METASTASIS WITH GENOMIC AND EPIGENOMIC BIOMARKERS

(71) Applicant: THE TRANSLATIONAL GENOMICS RESEARCH INSTITUTE, Phoenix, AZ (US)

(72) Inventor: Bodour Salhia, Mesa, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 15/494,426

(22) Filed: Apr. 21, 2017

(65) Prior Publication Data

US 2017/0292163 A1  Oct. 12, 2017

Related U.S. Application Data

(63) Continuation of application No. 14/262,732, filed on Apr. 26, 2014, now abandoned.

(60) Provisional application No. 61/913,176, filed on Dec. 6, 2013, provisional application No. 61/862,452, filed on Aug. 5, 2013, provisional application No. 61/816,591, filed on Apr. 26, 2013.

(51) Int. Cl.
  *C07H 21/04*  (2006.01)
  *C12Q 1/68*  (2018.01)
  *C12Q 1/6886*  (2018.01)

(52) U.S. Cl.
  CPC ...... *C12Q 1/6886* (2013.01); *C12Q 2600/112* (2013.01); *C12Q 2600/154* (2013.01)

(58) Field of Classification Search
  None
  See application file for complete search history.

(56) References Cited

U.S. PATENT DOCUMENTS

2013/0102483 A1\* 4/2013 Dimitrova ............ C12Q 1/6886
                                                                  506/9

OTHER PUBLICATIONS

Fang et al. (Science Translational Medicine, vol. 3, No. 75, pp. 1-11, Mar. 23, 2011). (Year: 2011).\*
Salhia et al. (Molecular Cancer Therapeutics, vol. 10, No. 11, Suppl 1, Abstract No. B198, Nov. 12-16, 2011, Conference). (Year: 2011).\*
Maher EA, et al. Brain metastasis: opportunities in basic and translational research. Cancer Res. 2009;69:6015-20.
Tosoni A, et al. Chemotherapy in breast cancer patients with brain metastases: have new chemotherapic agents changed the clinical outcome? Crit Rev Oncol Hematol. 2008;68:212-21.
Weil RJ, et al. Breast cancer metastasis to the central nervous system. Am J Pathol. 2005;167:913-20.
Gori S, et al. Central nervous system metastases in HER-2 positive metastatic breast cancer patients treated with trastuzumab: incidence, survival, and risk factors. Oncologist. 2007;12:766-73.
Kennecke H, et al. Metastatic behavior of breast cancer subtypes. J Clin Oncol. 2010;28:3271-7.
Merico D, et al. Visualizing gene-set enrichment results using the Cytoscape plug-in enrichment map. Methods Mol Biol. 2011;781:257-77.
Chen J, et al. ToppGene Suite for gene list enrichment analysis and candidate gene prioritization. Nucleic Acids Res. 2009;37:W305-11.
Wang C, et al. Genomic alterations in primary breast cancers compared with their sentinel and more distal lymph node metastases: an aCGH study. Genes Chromosomes Cancer. 2009;48:1091-101.
Nikolsky Y, et al. Genome-wide functional synergy between amplified and mutated genes in human breast cancer. Cancer research. 2008;68:9532-40.
Yao J, et al. Combined cDNA array comparative genomic hybridization and serial analysis of gene expression analysis of breast tumor progression. Cancer Res. 2006;66:4065-78.
El Gammal AT, et al. Chromosome 8p deletions and 8q gains are associated with tumor progression and poor prognosis in prostate cancer. Clin Cancer Res. 2010;16:56-64.
Raeder MB, et al. Integrated Genomic Analysis of the 8q24 Amplification in Endometrial Cancers Identifies ATAD2 as Essential to MYC-Dependent Cancers. PLoS One. 2013;8:e54873.
Ciro M, et al. ATAD2 is a novel cofactor for MYC, overexpressed and amplified in aggressive tumors. Cancer research. 2009;69:8491-8.
Wang J, et al. Derlin-1 is overexpressed in human breast carcinoma and protects cancer cells from endoplasmic reticulum stress-induced apoptosis. Breast cancer research : BCR. 2008;10:R7.
Wang S, et al. Nek2A contributes to tumorigenic growth and possibly functions as potential therapeutic target for human breast cancer. J Cell Biochem. 2012;113:1904-14.
Ishiwata T, et al. HSPB2 is dispensable for the cardiac hypertrophic response but reduces mitochondrial energetics following pressure overload in mice. PLoS One. 2012;7:e42118.
Benjamin IJ, et al. CRYAB and HSPB2 deficiency alters cardiac metabolism and paradoxically confers protection against myocardial ischemia in aging mice. Am J Physiol Heart Circ Physiol. 2007;293:H3201-9.
Baysal BE, et al. A high-resolution integrated map spanning the SDHD gene at 11q23: a 1.1-Mb BAC contig, a partial transcript map and 15 new repeat polymorphisms in a tumour-suppressor region. Eur J Hum Genet. 2001;9:121-9.

(Continued)

*Primary Examiner* — Jeanine A Goldberg

(57) ABSTRACT

The present invention provides a method of diagnosing a breast cancer central nervous system (CNS) metastasis in a subject, comprising determining the expression level of at least one biomarker in a subject-derived brain or breast tissue comparing the subject-derived expression level with a normal control level obtained from normal brain or breast cells; and correlating an increase or decrease of the subject-derived expression level as compared to the normal control level to a diagnosis of a breast cancer CNS metastasis. The present invention also provides a method for the treatment of a breast cancer CNS metastasis in a subject comprising administering to the subject an inhibitor of an overexpressed gene associated with CNS metastasis.

20 Claims, 19 Drawing Sheets

Specification includes a Sequence Listing.

(56) References Cited

OTHER PUBLICATIONS

Craig DW, et al. Genome and transcriptome sequencing in prospective metastatic triple-negative breast cancer uncovers therapeutic vulnerabilities. Mol Cancer Ther. 2013;12:104-16.
Ehrlich M, DNA methylation in cancer: too much, but also too little. Oncogene. 2002;21:5400-13.
Cancer Genome Atlas Network. Comprehensive molecular portraits of human breast tumours. Nature. 2012;490:61-70.
Hamilton A, et al. Role of the systemic immune system in brain metastasis. Mol Cell Neurosci. 2013;53:42-51.
Perou CM, et al. Molecular portraits of human breast tumours. Nature. 2000;406:747-52.
Perou CM, et al. Clinical implementation of the intrinsic subtypes of breast cancer. Lancet Oncol. 2010;11:718-9; author reply 20-1.
Parker JS, et al. Supervised risk predictor of breast cancer based on intrinsic subtypes. J Clin Oncol. 2009;27:1160-7.
Smid M, et al. Subtypes of breast cancer show preferential site of relapse. Cancer research. 2008;68:3108-14.
Shao MM, et al. A subset of breast cancer predisposes to brain metastasis. Med Mol Morphol. 2011;44:15-20.
Hoefnagel LD, et al. Receptor conversion in distant breast cancer metastases. Breast cancer research : BCR. 2010;12:R75.
Olshen AB, et al. Circular binary segmentation for the analysis of array-based DNA copy number data. Biostatistics. 2004;5:557-72.
Mermel CH, et al. GISTIC2.0 facilitates sensitive and confident localization of the targets of focal somatic copy-number alteration in human cancers. Genome Biol. 2011;12:R41.
Fang, F. et al. Breast Cancer Methylomes Establish an Epigenomic Foundation for Metastasis. Science Translational Medicine 3(75):1-11, Mar. 23, 2011.
Salhia et al. Integrated genomic analysis of breast cancer CNS metastasis to the CNS. Molecular Cancer Therapeutics. vol. 10, No. 11, Suppl 1, Abstract No. 8198, Nov. 12-16, 2011(Conference).
Harrell JC et al. Genomic analysis identifies unique signatures predictive of brain, lung, and liver relapse. Breast cancer research and treatment. 2012; 132: 523-535.
Weigelt B. et al. Molecular portraits and 70-gene prognosis signature are preserved throughout the metastatic process of breast cancer. Cancer research Oct. 15, 2005;65(20):9155-8.

* cited by examiner

A

A

B

C

D

E

F

A

METHODS OF DETECTING BREAST CANCER BRAIN METASTASIS WITH GENOMIC AND EPIGENOMIC BIOMARKERS

CROSS-REFERENCE TO RELATED APPLICATIONS

The present application is a Continuation of U.S. patent application Ser. No. 14/262,732, filed on Apr. 26, 2014 (published as US 20140322243), which claims the benefit of U.S. Provisional Patent Application Nos. 61/913,176 filed on Dec. 6, 2013; 61/862,452 filed on Aug. 5, 2013; and 61/816,591 filed on Apr. 26, 2013, each of which is incorporated herein by reference in their entireties.

TECHNICAL FIELD

This application relates to the field of cancer diagnostics and therapeutic agents and specifically to methods of diagnosing and treating breast cancer CNS metastasis.

REFERENCE TO SEQUENCE LISTING SUBMITTED ELECTRONICALLY

The official copy of the sequence listing is submitted electronically via EFS-Web as an ASCII-formatted sequence listing with a file named "91482_133_Sequence_Listing.txt" created on Apr. 16, 2014, and having a size of 2,535 bytes, and is filed concurrently with the specification. The sequence listing contained in this ASCII-formatted document is part of the specification and is herein incorporated by reference in its entirety.

BACKGROUND

Brain metastasis is the most common intracranial tumor, occurring in 15-40% of all cancer patients with metastatic disease [1,2,3]. The incidence of brain metastasis has increased in recent years, possibly due to prolonged survival of cancer patients receiving aggressive treatments for their primary or systemic disease [1,2,3]. Given their overall frequency in the population, lung and breast cancer are by far the most common tumors to develop brain metastases [1,2,3].

Epidemiological studies suggest that brain metastases occur with a frequency of approximately 10-16% in patients with breast cancer, although large autopsy studies indicate that frequencies may be as high as 18-30% [2,3,4,5]. Brain metastases occur rapidly, usually within 2-3 years following diagnosis of systemic metastatic disease, and the median survival once there is brain involvement is a stifling 13 months with fewer than 2% of patients surviving greater than 2 years. Breast cancer involving the brain (parenchyma or leptomeninges) is considered a feature of late-stage progressive disease for which few effective treatments exist. Due to limitations imposed by the blood brain barrier (BBB), chemotherapy has not generally been used to treat most epithelial cancers that metastasize to the brain. Whole brain radiation can provide a survival benefit of 4-5 months, which can be further extended with stereotactic radiosurgery (SRS). Surgery can also lead to dramatic improvements in survival if fewer than 3 metastases exist and all are treated aggressively with surgery or SRS.

Currently there are few predictive measures for identification of patients at risk for developing brain metastasis from their primary cancer. In general, the development of brain metastases from breast cancer depends on several prognostic factors, including younger age, ethnicity, hormone receptor negative status, presence of BRCA1 germline mutations and the expression of the epidermal growth factor receptor 2 (Her2/neu) proto-oncogene, all of which contribute to an increased rate of brain metastasis [2].

There is a need to identify genomic and epigenomic biomarkers in breast cancer brain metastases to understand the landscape of breast cancer brain metastatic lesions. These biomarkers would allow for earlier diagnosis of breast cancer brain metastases and the development of new therapeutic targets to control this fatal manifestation of breast cancer.

SUMMARY

The present invention provides a method for diagnosing a breast cancer central nervous system (CNS) metastasis in a subject, comprising: a) determining the expression level of at least one gene selected from the group consisting of ATAD2, BRAF, DERL1, DNMTRB, NEK2A, AKT1, AURKA, AURKB, ESR2, FASN, FOXM1, TBX2, TNFRSF12A, PSENEN, HIF1A, IGF1R, MCL1, PPFIA1, RAF1, PRL, RXRA, SRD5A2, SUMO2, TYMS, UBA1, VEGFA, WNT3A, HOXA7, HOXA9, HOXA10, HOXA11, ERBB2, NEUROD2, and WNT9A in a subject-derived brain or breast tissue; b) comparing the subject-derived expression level determined in step a) with a normal control level obtained from normal brain or breast cells; and c) correlating an increase of said subject-derived expression level as compared to the normal control level to a diagnosis of a breast cancer CNS metastasis.

In some embodiments, gene expression is determined with quantitative reverse-transcriptase (RT)-PCR. In certain aspects, the quantitative RT-PCR comprises amplification of nucleic acids from the breast or brain tissue with a primer comprising a sequence selected from the group consisting of SEQ ID NO:1, SEQ ID NO:2, SEQ ID NO:3, SEQ ID NO:4, SEQ ID NO:5, and SEQ ID NO:6.

In another embodiment, the present invention provides a method for diagnosing a breast cancer CNS metastasis in a subject, comprising: a) determining the expression level of at least one gene selected from the group consisting of CTNNA3, ATM, TCF4, CDKN2A, CDKN2B, MSH6, RB1, RPS6KA3, CRYAB, HSPB2, and DMRTA1 in a subject-derived brain or breast tissue; b) comparing the subject-derived expression level determined in step a) with a normal control level obtained from normal brain or breast cells; and c) correlating a decrease of said subject-derived expression level as compared to the normal control level to a diagnosis of a breast cancer CNS metastasis.

In yet another embodiment, the present invention provides a method for the treatment of a breast cancer CNS metastasis in a subject comprising administering to the subject an inhibitor of a gene selected from the group consisting of ATAD2, BRAF, DERL1, DNMTRB, NEK2A, AKT1, AURKA, AURKB, ESR2, FASN, FOXM1, TBX2, TNFRSF12A, PSENEN, HIF1A, IGF1R, MCL1, PPFIA1, RAF1, PRL, RXRA, SRD5A2, SUMO2, TYMS, UBA1, VEGFA, WNT3A, HOXA7, HOXA9, HOXA10, HOXA11, ERBB2, NEUROD2, and WNT9A. The inhibitor may be any one of a chemical agent, an antibody, and an siRNA molecule.

In certain aspects, the present invention is directed to a method for the treatment of a breast cancer CNS metastasis in a subject comprising administering to the subject at least one compound selected from the group consisting of Vidaza, Entinostat, and a PARP inhibitor. The PARP inhibitor may be any one of Iniparib, Olaparib, Rucaparib, Veliparib, CEP 9722, MK 4827, BMN-673, and 3-aminobenzamide. In some embodiments, Vidaza and the PARP inhibitor are administered in combination or sequentially to the subject.

In other aspects, the present invention provides a method for diagnosing a breast cancer CNS metastasis in a subject, comprising: a) determining the methylation level of at least one gene selected from the group consisting of EDNRB, RUNX3, RELN, BANK1, CDKN1, ITGAM, EDN3, and PENK in a subject-derived brain or breast tissue; b) comparing the subject-derived methylation level determined in step a) with a normal control level obtained from normal brain or breast cells; and c) correlating an increase of said subject-derived methylation level as compared to the normal control level to a diagnosis of a breast cancer CNS metastasis. In certain aspects, the methylation level is determined with bisulfite pyrosequencing.

In another embodiment, the present invention provides s method for diagnosing a breast cancer CNS metastasis in a subject, comprising: a) determining the methylation level of at least one gene selected from the group consisting of KRT8, ALDH1A3, FANCG, TRIM29 and HOXA11 in a subject-derived brain or breast tissue; b) comparing the subject-derived methylation level determined in step a) with a normal control level obtained from normal brain or breast cells; and c) correlating a decrease of said subject-derived methylation level as compared to the normal control level to a diagnosis of a breast cancer CNS metastasis.

In certain embodiments, prior to diagnosis of a breast cancer CNS metastasis, the subject has been diagnosed with a breast cancer molecular subtype of Luminal A, Luminal B, basal-like, normal-like, or Her2+/ER−.

In certain aspects, the methylation levels of genes in subject-derived brain or breast tissue are determined with bisulfite treatment of DNA, reverse phase high pressure liquid chromatography (HPLC), methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, methylation detection after restriction, methylation-sensitive restriction fingerprinting, restriction landmark genomic scanning (RLGS), or bisulfite conversion combined with bisulfite restriction analysis (COBRA).

BRIEF DESCRIPTION OF THE DRAWINGS

FIG. 2A: Hierarchical clustering of 863 genes distinguishing breast brain metastases (BBM) from non-neoplastic breast (NBr) and non-neoplastic brain tissue (NBn); FIG. 2B: Cell Cycle Gene Network. Genes that mapped to the 'Cell Cycle' categories were used to construct a direct interaction network; FIG. 2C: DNA Repair Network. Genes that mapped to the 'DNA Repair' category were used to construct a direct interaction network. Two DNA repair processes are highlighted and connected to genes annotated to those processes. For FIGS. 2B and 2C the gene nodes are shaded in proportion to the degree of upregulation. Gene nodes are upregulated unless otherwise labeled as downregulated. Log 2 ratios are listed under the individual nodes. Direct physical interaction relationships are represented by solid lines. Dotted lines represents indirect physical interactions; FIG. 2D: GSEA Enrichment Map. The results from the GSEA analysis comparing 35 breast cancer brain metastases to 10 non-tumor brain and 10 non-tumor breast were visualized using Cytoscape and Enrichment Map plugin. The significant gene sets from the CS gene ontology library are represented with a p-value of: SO.OS and false discovery rate (Q) of 0.5. Each individual node represents one gene set with the size of node proportional to number of genes in the set and shading intensity relates to degree of enrichment (up in tumor; down in tumor). The relative overlap of the number of genes shared by individual nodes is represented by the thickness of the connecting edges. Interesting subgroups in the network are circled and manually annotated; FIG. 2E: Vertical scatter plots showing FOXM1 and AURKB overexpression by qRT-PCR in breast brain metastasis (BBM, n=42) compared to early stage primary breast tumors (n=50). Fold expression was relative to expression in non-neoplastic breast or brain samples (n=10).

FIG. 4A: Hierarchical clustering showing 425 tumor-specific differentially methylated loci (DML). Breast brain metastases (BBM) are distinguished from non-neoplastic breast (NBr) and non-neoplastic brain tissue (NBn). FIG. 4B: Box plot demonstrating higher overall median methylation levels for 425 DML in BBM compared with NBr and NBn. FIG. 4C: Hierarchical clustering of 90 DML obtained by performing an ANOVA analysis and analyzing the union of genes between the different subtypes was able to distinguish BBM intrinsic subtype; FIG. 4D: Box plot representing the median methylation levels of 90 DML described above. NBr and NBn values are also shown. Basal-like breast brain metastases have overall lower methylation compared with the other groups. FIG. 4E: CpG Island Hypomethylator Phenotype (CIHMP) in basal-like brain metastases representing the 15 most hypomethylated CpG Island loci when compared to Luminal B and Her2+/ER− tumors; FIG. 4F: Box plot graphing the methylation values of the 15 CpG loci most hypomethylated in basal-like breast brain metastases.

DETAILED DESCRIPTION

Figure 1:
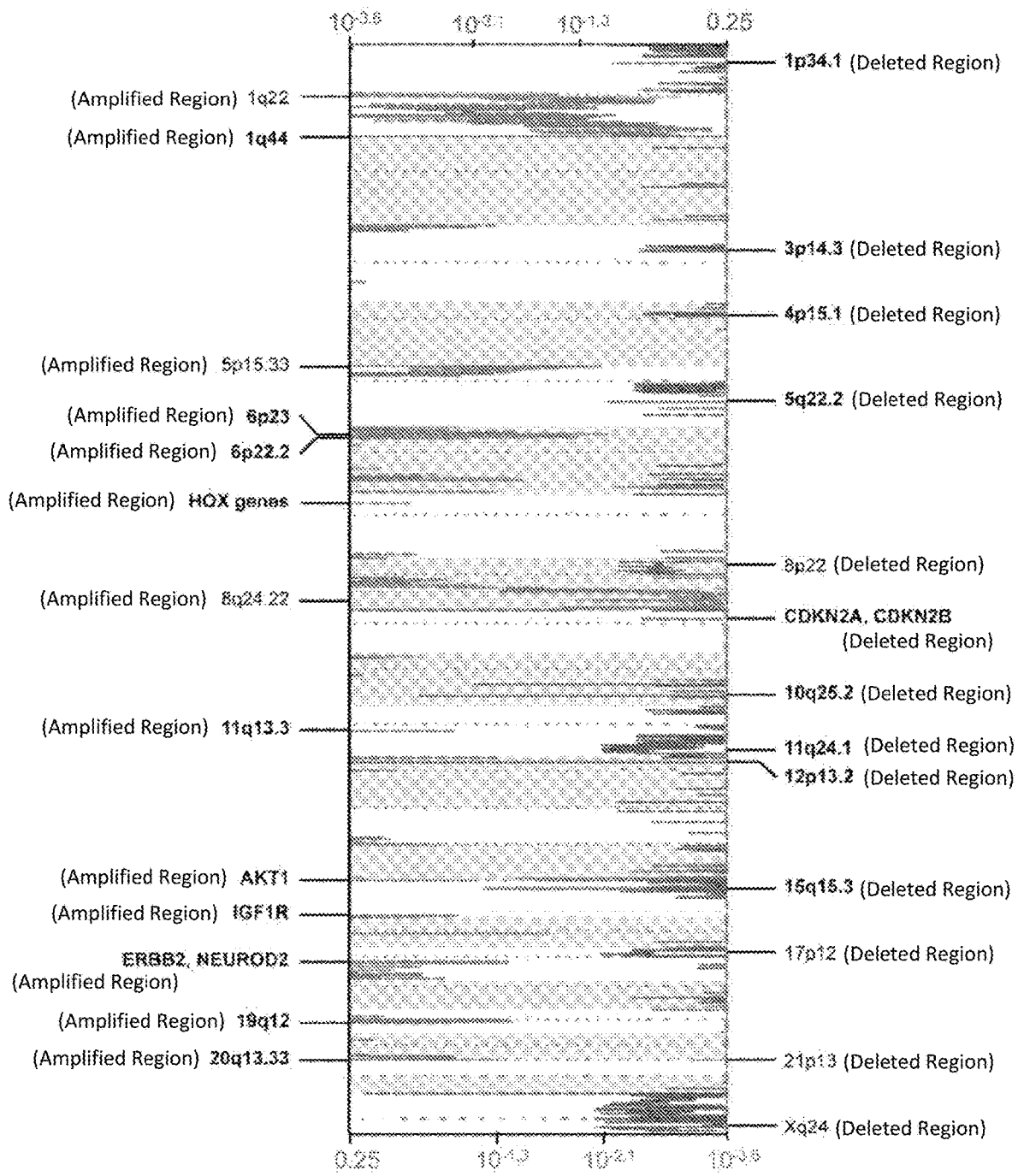
FIG. 1 depicts DNA copy number analysis of breast brain metastasis. GISTIC analysis was conducted on Agilent SurePrint G3 Human CGH Microarray data for 15 breast brain metastases. Significant false discovery rates (Q-values) for amplified and deleted regions are plotted genome-wide. Annotations for a few of the significant regions are shown. Focal amplifications and deletions are annotated in boldface, and broad amplifications and deletions are annotated in non-boldface. Q values for deleted and amplified genes are displayed along the x-axis on top and bottom of the figure, respectively.

The present invention is directed to methods of diagnosing and treating breast cancer CNS metastasis. In certain aspects, the diagnostic methods comprise an analysis of gene expression and/or the methylation state of at least one gene. Gene expression may be analyzed by polymerase chain reaction.

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions (Mg2+); and monovalent cation potassium ions.

PCR technology relies on thermal strand separation followed by thermal dissociation. During this process, at least one primer per strand, cycling equipment, high reaction temperatures and specific thermostable enzymes are used (U.S. Pat. Nos. 4,683,195 and 4,883,202). Alternatively, it is possible to amplify the DNA at a constant temperature (Nucleic Acids Sequence Based Amplification (NASBA) Kievits, T., et al., J. Virol Methods, 1991; 35, 273-286; and Malek, L. T., U.S. Pat. No. 5,130,238; T7 RNA polymerase-mediated amplification (TMA) (Giachetti C, et al. J Clin Microbiol 2002 July; 40(7):2408-19; or Strand Displacement Amplification (SDA), Walker, G. T. and Schram, J. L., European Patent Application Publication No. 0 500 224 A2; Walker, G. T., et al., Nuc. Acids Res., 1992; 20, 1691-1696).

Thermal cycling subjects the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step—94-96° C.; denaturation step—94-98° C.; annealing step—50-65° C.; extension/elongation step—70-74° C.; final elongation—70-74° C.; final hold—4-10° C.

Real-time polymerase chain reaction, also called quantitative real time polymerase chain reaction (QRT-PCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

Amplified nucleic acid can be detected using a variety of detection technologies well known in the art. For example, amplification products may be detected using agarose gel by performing electrophoresis with visualization by ethidium bromide staining and exposure to ultraviolet (UV) light, by sequence analysis of the amplification product for confirmation, or hybridization with an oligonucleotide probe.

The oligonucleotide probe may comprise a flourophore and/or a quencher. The oligonucleotide probe may also contain a detectable label including any molecule or moiety having a property or characteristic that is capable of detection, such as, for example, radioisotopes, fluorophores, chemiluminophores, enzymes, colloidal particles, and fluorescent microparticles.

Probe sequences can be employed using a variety of methodologies to detect amplification products. Generally all such methods employ a step where the probe hybridizes to a strand of an amplification product to form an amplification product/probe hybrid. The hybrid can then be detected using labels on the primer, probe or both the primer and probe. Examples of homogeneous detection platforms for detecting amplification products include the use of FRET (fluorescence resonance energy transfer) labels attached to probes that emit a signal in the presence of the target sequence. "TaqMan" assays described in U.S. Pat. Nos. 5,210,015; 5,804,375; 5,487,792 and 6,214,979 (each of which is herein incorporated by reference) and Molecular Beacon assays described in U.S. Pat. No. 5,925,517 (herein incorporated by reference) are examples of techniques that can be employed to detect nucleic acid sequences. With the "TaqMan" assay format, products of the amplification reaction can be detected as they are formed or in a so-called "real time" manner. As a result, amplification product/probe hybrids are formed and detected while the reaction mixture is under amplification conditions.

For example, the PCR probes may be TaqMan™ probes that are labeled at the 5' end with a fluorophore and at the 3'-end with a quencher molecule. Suitable fluorophores and quenchers for use with TaqMan® probes are disclosed in U.S. Pat. Nos. 5,210,015, 5,804,375, 5,487,792 and 6,214, 979 and WO 01/86001 (Biosearch Technologies). Quenchers may be Black Hole Quenchers disclosed in WO 01/86001.

Nucleic acid hybridization can be done using techniques and conditions known in the art. Specific hybridization conditions will depend on the type of assay in which hybridization is used. Hybridization techniques and conditions can be found, for example, in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York) and Sambrook et al. (1989) Molecular Cloning. A Laboratory Manual (2d ed., Cold Spring Harbor Laboratory Press, Plainview, N.Y.).

Hybridization of nucleic acid may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified. Alternatively, stringency conditions can be adjusted to allow some mismatching in sequences so that lower degrees of similarity are detected.

It is understood in the art that a nucleic acid molecule need not be 100% complementary to a target nucleic acid sequence to be specifically hybridizable. That is, two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30 degrees C. for short probes (e.g., 10 to 50 nucleotides) and at least about 60 degrees C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37 degrees C., and a wash in 1.times. to 2 times.SSC (20.times.SSC=3.0 M NaCl/0.3 M trisodium citrate) at 50 to 55.degree. C. Exemplary moderate stringency conditions include hybridization in 40 to 45% formamide, 1.0 M NaCl, 1% SDS at 37 degrees C., and a wash in 0.5.times. to 1.times SSC at 55 to 60.degree. C. Exemplary high stringency conditions include hybridization in 50% formamide, 1 M NaCl, 1% SDS at 37 degrees C., and a wash in 0.1.times.SSC at 60 to 65 degrees C. The duration of hybridization is generally less than about 24 hours, usually about 4 to about 12 hours, or less depending on the assay format.

It should be noted that the oligonucleotides of this disclosure can be used as primers or probes, depending on the intended use or assay format. For example, an oligonucleotide used as a primer in one assay can be used as a probe in another assay. The grouping of the oligonucleotides into primer pairs and primer/probe sets reflects certain implementations only. However, the use of other primer pairs comprised of forward and reverse primers selected from different preferred primer pairs is specifically contemplated.

Quantitative Real-Time PCR (qPCR) Detection Chemistries

There are several commercially available nucleic acid detection chemistries currently used in qPCR. These chemistries include DNA binding agents, FRET based nucleic acid detection, hybridization probes, molecular beacons, hydrolysis probes, and dye-primer based systems. Each of these chemistries is discussed in more detail below.

DNA Binding Agents

The first analysis of kinetic PCR was performed by Higuchi et al. who used ethidium bromide to bind double-stranded DNA products (U.S. Pat. No. 5,994,056; U.S. Published Application No. 2001/6171785). Ethidium bromide, like all other DNA binding agents used in kinetic PCR, is able to increase in fluorescent intensity upon binding. The resulting increase in signal can be recorded over the course of the reaction, and plotted versus the cycle number. Recording the data in this way is more indicative of the initial concentration of the sample of interest compared to end-point analysis.

Binding dyes are relatively inexpensive as compared to other detection chemistries. The advantages of using these binding dyes are their low cost and excellent signal to noise ratios. Disadvantages include their non-specific binding properties to any double-stranded DNA in the PCR reaction, including amplicons created by primer-dimer formations. In order to confirm the production of a specific amplicon, a melting curve analysis should be performed. Another drawback is that amplification of a longer product will generate more signal than a shorter one. If amplification efficiencies are different, quantification may be even more inaccurate.

SYBR® Green I from Invitrogen™ (Carlsbad, Calif.) is a popular intercalating dye. SYBR® Green I is a cyclically substituted asymmetric cyanine dye (U.S. Pat. Nos. 5,436, 134; 5,658,751). A minor groove binding asymmetric cyanine dye known as BEBO, has been used in real-time PCR. BEBO causes a non-specific increase in fluorescence with time, perhaps due to a slow aggregation process and is less sensitive compared to SYBR® Green I. A similar dye called BOXTO has also been reported for use in qPCR (U.S. Published Application No. 2006/0211028). Like BEBO, BOXTO is less sensitive than SYBR® Green I (U.S. Published Application No. 2006/0211028).

Other common reporters include YO-PRO-1 and thiazole orange (TO) which are intercalating asymmetric cyanine dyes. While these dyes exhibit large increases in fluorescence intensity upon binding, TO and Oxazole Yellow (YO) have been reported to perform poorly in real-time PCR. Other dyes that may be used include, but are not limited to, pico green, acridinium orange, and chromomycin A3 (U.S. Published Application No. 2003/6569627). Dyes that may be compatible with real-time PCR can be obtained from various vendors such as, Invitrogen, Cambrex Bio Science (Walkersville, Md.), Rockland Inc. (Rockland, Me.), Aldrich Chemical Co. (Milwaukee, Wis.), Biotium (Hayward, Calif.), TATAA Biocenter AB. (Goteborg, Sweden) and Idaho Technology (Salt Lake City, Utah) (U.S. Published Application No. 2007/0020672).

A dye known as EvaGreen™ (Biotium) has shown promise in that it is designed to not inhibit PCR, and is more stable in alkaline conditions as compared to SYBR® Green I (U.S. Published Application No. 2006/0211028). Other newer dyes include the LCGreen® dye family (Idaho Technology). LCGreen® I and LCGreen® Plus are the most commercially competitive of these dyes. LCGreen® Plus is considerably brighter than LCGreen® (U.S. Published Application No. 2007/0020672; Dorak, 2006; U.S. Published Application No. 2005/0233335; U.S. Published Application No. 2066/0019253).

FRET Based Nucleic Acid Detection

Many real-time nucleic acid detection methods utilize labels that interact by Förster Resonance Energy Transfer (FRET). This mechanism involves a donor and acceptor pair wherein the donor molecule is excited at a particular wavelength, and subsequently transfers its energy non-radiatively to the acceptor molecule. This typically results in a signal change that is indicative of the proximity of the donor and acceptor molecules to one another.

Early methods of FRET based nucleic acid detection that lay a foundation for this technology in general, include work by Heller et al. (U.S. Pat. Nos. 4,996,143; 5,532,129; and 5,565,322, which are incorporated by reference). These patents introduce FRET based nucleic acid detection by including two labeled probes that hybridize to the target sequence in close proximity to each other. This hybridization event causes a transfer of energy to produce a measurable change in spectral response, which indirectly signals the presence of the target.

Cardullo et al., Proc. Natl. Acad. Sci. USA, 85:8790-8804, 1988. (incorporated by reference) established that fluorescence modulation and nonradiative fluorescence resonance energy transfer can detect nucleic acid hybridization in solution. This study used three FRET based nucleic acid detection strategies. The first includes two 5' labeled probes that were complementary to one another, allowing transfer to occur between a donor and acceptor fluorophore over the length of the hybridized complex. In the second method, fluorescent molecules were covalently attached to two nucleic acids, one at the 3' end and the other at the 5' end. The fluorophore-labeled nucleic acids hybridized to distinct but closely spaced sequences of a longer, unlabeled nucleic acid. Finally, an intercalating dye was used as a donor for an acceptor fluorophore that was covalently attached at the 5' end of the probe.

Morrison et al., Biochemistry, 32:3095-3104, 1993, incorporated by reference, used complementary labeled probes to detect unlabeled target DNA by competitive hybridization, producing fluorescence signals which increased with increasing target DNA concentration. In this instance, two probes were used that were complementary to one another and labeled at their 5' and 3' ends with fluorescein and fluorescein quencher, respectively. Later work also showed that fluorescence melting curves could be used to monitor hybridization.

Hybridization Probes

Hybridization probes used in real-time PCR were developed mainly for use with the Roche LightCycler® instruments (U.S. Published Application No. 2001/6174670; U.S. Published Application No. 2000/6140054). These are sometimes referred to as FRET probes, LightCycler® probes, or dual FRET probes.

Hybridization probes are used in a format in which FRET is measured directly. Each of the two probes is labeled with a respective member of a fluorescent energy transfer pair, such that upon hybridization to adjacent regions of the target DNA sequence, the excitation energy is transferred from the donor to the acceptor, and subsequent emission by the acceptor can be recorded as reporter signal. The two probes anneal to the target sequence so that the upstream probe is fluorescently labeled at its 3' end and the downstream probe is labeled at its 5' end. The 3' end of the downstream probe is typically blocked by phosphorylation or some other means to prevent extension of the probe during PCR. The dye coupled to the 3' end of the upstream probe is sufficient to prevent extension of this probe. This reporter system is different from other FRET based detection methods (molecular beacons, TaqMan®, etc.) in that it uses FRET to generate rather than to quench the fluorescent signal.

Typical acceptor fluorophores include the cyanine dyes (Cy3 and Cy5), 6-carboxy-4,7,2',7'-tetrachlorofluorescein (TET), 6-carboxy-N,N,N',N'-tetramethylrhodamine (TAMRA), and 6-carboxyrhodamine X (ROX). Donor fluorophores are usually 6-carboxyfluoroscein (FAM) (Wilhelm and Pingoud, 2003). Hybridization probes are particularly advantageous for genotyping and mismatch detection. Melting curve analysis can be performed in addition to the per-cycle monitoring of fluorescence during the PCR reaction. A slow heating of the sample after probe hybridization can provide additional qualitative information about the sequence of interest. Base-pair mismatches will shift the stability of a duplex, in varying amounts, depending on the mismatch type and location in the sequence.

Molecular Beacons

Molecular beacons, also known as hairpin probes, are stem-loop structures that open and hybridize in the presence of a complementary target sequence, typically causing an increase in fluorescence (U.S. Pat. No. 5,925,517); U.S. Published Application No. 2006/103476). Molecular beacons typically have a nucleic acid target complement sequence flanked by members of an affinity pair that, under assay conditions in the absence of target, interact with one another to form a stem duplex. Hybridization of the probes to their preselected target sequences produces a conformational change in the probes, forcing the "arms" apart and eliminating the stem duplex and thereby separating the fluorophore and quencher.

Hydrolysis Probes

Hydrolysis probes, also known as the TaqMan® assay (U.S. Pat. No. 5,210,015), are popular because they only involve a single probe per target sequence, as opposed to two probes (as in hybridization probes). This results in a cost savings per sample. The design of these probes is also less complicated than that of molecular beacons. These are typically labeled with a reporter on the 5' end and a quencher on the 3' end. When the reporter and quencher are fixed onto the same probe, they are forced to remain in close proximity. This proximity effectively quenches the reporter signal, even when the probe is hybridized to the target sequence. During the extension or elongation phase of the PCR reaction, a polymerase known as Taq polymerase is used because of its 5' exonuclease activity. The polymerase uses the upstream primer as a binding site and then extends. Hydrolysis probes are cleaved during polymerase extension at their 5' end by the 5'-exonuclease activity of Taq. When this occurs, the reporter fluorophore is released from the probe, and subsequently, is no longer in close proximity to the quencher. This produces a perpetual increase in reporter signal with each extension phase as the PCR reaction continues cycling. In order to ensure maximal signal with each cycle, hydrolysis probes are designed with a Tm that is roughly 10° C. higher than the primers in the reaction.

However, the process of cleaving the 5' end of the probe need not require amplification or extension of the target sequence (U.S. Pat. No. 5,487,972). This is accomplished by placing the probe adjacent to the upstream primer, on the target sequence. In this manner, sequential rounds of annealing and subsequent probe hydrolysis can occur, resulting in a significant amount of signal generation in the absence of polymerization. Uses of the real-time hydrolysis probe reaction are also described in U.S. Pat. Nos. 5,538,848 and 7,205,105, both of which are incorporated by references.

Dye-Primer Based Systems

There are numerous dye-labeled primer based systems available for real-time PCR. These range in complexity from simple hairpin primer systems to more complex primer structures where the stem-loop portion of the hairpin probe is attached via a non-amplifiable linker to the specific PCR primer. These methods have the advantage that they do not require an additional intervening labeled probe that is essential for probe-based assay systems and they also allow for multiplexing that is not possible with DNA binding dyes. However, the success of each of these methods is dependent upon careful design of the primer sequences.

Hairpin primers contain inverted repeat sequences that are separated by a sequence that is complementary to the target DNA (U.S. Pat. No. 5,866,336). The repeats anneal to form a hairpin structure, such that a fluorophore at the 5'-end is in close proximity to a quencher at the 3'-end, quenching the fluorescent signal. The hairpin primer is designed so that it will preferentially bind to the target DNA, rather than retain the hairpin structure. As the PCR reaction progresses, the primer anneals to the accumulating PCR product, the fluorophore and quencher become physically separated, and the level of fluorescence increases.

Invitrogen's LUX™ (Light Upon eXtension) primers are fluorogenic hairpin primers which contain a short 4-6 nucleotide extension at the 5' end of the primer that is complementary to an internal sequence near the 3' end and overlaps the position of a fluorophore attached near the 3' end. Basepairing between the complementary sequences forms a double-stranded stem which quenches the reporter dye that is in close proximity at the 3' end of the primer. During PCR, the LUX™ primer is incorporated into the new DNA strand and then becomes linearized when a new complementary second strand is generated. This structural change results in an up to 10-fold increase in the fluorescent signal. These primers can be difficult to design and secondary structure must be carefully analyzed to ensure that the probe anneals preferentially to the PCR product. Design and validation services for custom LUX™ primers are available from Invitrogen.

More recently, hairpin probes have become part of the PCR primer. In this approach, once the primer is extended, the sequence within the hairpin anneals to the newly synthesized PCR product, disrupting the hairpin and separating the fluorophore and quencher.

Scorpion® primers are bifunctional molecules in which an upstream hairpin probe sequence is covalently linked to a downstream primer sequence (U.S. Published Application No. 2001/6270967; U.S. Published Application No. 2005/0164219). The probe contains a fluorophore at the 5' end and a quencher at the 3' end. In the absence of the target, the probe forms a 6-7 base stem, bringing the fluorophore and quencher in close proximity and allowing the quencher to absorb the fluorescence emitted by the fluorophore. The loop portion of the scorpion probe section consists of sequence complementary to a portion of the target sequence within 11 bases downstream from the 3' end of the primer sequence. In the presence of the target, the probe becomes attached to the target region synthesized in the first PCR cycle. Following the second cycle of denaturation and annealing, the probe and the target hybridize. Denaturation of the hairpin loop requires less energy than the new DNA duplex produced. Thus, the scorpion probe loop sequence hybridizes to a portion of the newly produced PCR product, resulting in separation of the fluorophore from the quencher and an increase in the fluorescence emitted.

As with all dye-primer based methods, the design of Scorpion primers follows strict design considerations for secondary structure and primer sequence to ensure that a secondary reaction will not compete with the correct probing event. The primer pair should be designed to give an amplicon of approximately 100-200 bp. Ideally, the primers should have as little secondary structure as possible and should be tested for hairpin formation and secondary structures. The primer should be designed such that it will not hybridize to the probe element as this would lead to linearization and an increase in non-specific fluorescence emission. The Tm's of the two primers should be similar and the stem Tm should be 5-10° C. higher than the probe Tm. The probe sequence should be 17-27 bases in length and the probe target should be 11 bases or less from the 3' end of the scorpion. The stem sequence should be 6 to 7 bases in length and should contain primarily cytosine and guanine. The 5' stem sequence should begin with a cytosine as guanine may quench the fluorophore. Several oligonucleotide design software packages contain algorithms for Scorpion primer design and custom design services are available from some oligonucleotide vendors as well.

The Plexor™ system from Promega is a real-time PCR technology that has the advantage that there are no probes to design and only one PCR primer is labeled (U.S. Pat. No. 5,432,272; U.S. Published Application No. 2000/6140496; U.S. Published Application No. 2003/6617106). This technology takes advantage of the specific interaction between two modified nucleotides, isoguanine (iso-dG) and 5'-methylisocytosine (iso-dC). Main features of this technology are that the iso-bases will only base pair with the complementary iso-base and DNA polymerase will only incorporate an iso-base when the corresponding complementary iso-base is present in the existing sequence. One PCR primer is synthesized with a fluorescently-labeled iso-dC residue as the 5'-terminal nucleotide. As amplification progresses, the labeled primer is annealed and extended, becoming incorporated in the PCR product. A quencher-labeled iso-dGTP (dabsyl-iso-dGTP), available as the free nucleotide in the PCR master mix, specifically base pairs with the iso-dC and becomes incorporated in the complementary PCR strand, quenching the fluorescent signal. Primer design for the Plexor system is relatively simple as compared to some of the other dye-primer systems and usually follows typical target-specific primer design considerations. A web-based Plexor Primer Design Software, available from Promega, assists in selecting the appropriate dye and quencher combinations, and provides links to oligonucleotide suppliers licensed to provide iso-base containing primers.

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

Methods of Determining DNA Methylation Levels

In the method of the invention, determining that gene expression is absent or low relative to a control may be considered to be evidence that the gene is methylated such that transcription of the gene (and thus translation of the protein) is inhibited. It will be recognized by those skilled in the art that a determination of gene expression that is absent or low relative to a control can be related to methylation status of the gene if desired by more direct analysis of the methylation status of the gene using any suitable method. Some non-limiting examples of suitable methods for analyzing DNA methylation include bisulfite treatment of DNA, reverse phase high pressure liquid chromatography (HPLC), methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfite pyrosequencing, methylation detection after restriction, methylation-sensitive restriction fingerprinting, restriction landmark genomic scanning (RLGS), and bisulfite conversion combined with bisulfite restriction analysis (COBRA).

In one embodiment, bisulfite treatment, is used. The bisulfate method is used to convert unmethylated cytosines to uracil. The bisulfite treated DNA may be amplified and sequenced to determine the methylation status of CpG sites, where uracil is read as thymine (T) in the sequence of the amplified DNA when methylation is not present. However, since methylated cytosines are not converted to uracil by bisulfite treatment, they are read as cytosine (C), when analyzing methylated DNA.

In some embodiments, identifying increased methylation levels of at least one gene selected from the group consisting of EDNRB, RUNX3, RELN, BANK1, CDKN1, ITGAM, EDN3, and PENK in a subject-derived brain or breast tissue compared to a normal control level obtained from normal brain or breast cells indicates that the subject is a candidate for receiving a DNA methylation inhibitor Methods of Treating Breast Cancer CNS Metastasis In certain aspects, the present invention provides methods of treatment of a breast cancer CNS metastasis in a subject. The method of treatment may comprise administration of Vidaza, Entinostat, and/or PARP inhibitors to the subject.

Azacitidine (INN) or 5-azacytidine, sold under the trade name Vidaza, is a chemical analogue of cytidine, a nucleoside present in DNA and RNA. Azacitidine and its deoxy derivative, decitabine (also known as 5-aza-2'deoxycytidine), are used in the treatment of myelodysplastic syndrome. Both drugs were first synthesized in Czechoslovakia as potential chemotherapeutic agents for cancer. Vidaza can be used to remove methyl groups from DNA. This may weaken the effects of gene silencing mechanisms that occurred prior to the methylation. Methylation events are therefore believed to secure the DNA in a silenced state. Demethylation may reduce the stability of silencing signals and thus confer relative gene activation.

Entinostat, also known as SNDX-275 and MS-275, is a benzamide histone deacetylase inhibitor undergoing clinical trials for treatment of various cancers. Entinostat inhibits class I HDAC1 and HDAC3 with $IC_{50}$ of 0.51 µM and 1.7 µM, respectively.

PARP inhibitors are a group of pharmacological inhibitors of the enzyme poly ADP ribose polymerase (PARP). They are developed for multiple indications; the most important is the treatment of cancer. Several forms of cancer are more dependent on PARP than regular cells, making PARP an attractive target for cancer therapy. PARP1 is a protein that is important for repairing single-strand breaks ('nicks' in the DNA). If such nicks persist unrepaired until DNA is replicated (which must precede cell division), then the replication itself can cause double strand breaks to form. Drugs that inhibit PARP1 cause multiple double strand breaks to form in this way, and in tumours with BRCA1, BRCA2 or PALB2 mutations these double strand breaks cannot be efficiently repaired, leading to the death of the cells. Normal cells that do not replicate their DNA as often as cancer cells, and that lacks any mutated BRCA1 or BRCA2 still have homologous repair operating, which allows them to survive the inhibition of PARP.

In one embodiment, the method for treating cancer may include administering a pharmaceutical composition that includes a pharmaceutically acceptable carrier and a therapeutically effective amount of a substance that targets and inhibits ATAD2, BRAF, DERL1, DNMTRB, NEK2A, AKT1, AURKA, AURKB, ESR2, FASN, FOXM1, TBX2, TNFRSF12A, PSENEN, HIF1A, IGF1R, MCL1, PPFIA1, RAF1, PRL, RXRA, SRD5A2, SUMO2, TYMS, UBA1, VEGFA, WNT3A, HOXA7, HOXA9, HOXA10, HOXA11, ERBB2, NEUROD2, or WNT9A expression or activity for the targeted biologic therapy. In another embodiment, the pharmaceutical composition may also include a therapeutically effective amount of a substance that targets a receptor for the targeted biologic therapy.

In one embodiment, the inhibitor may include any suitable substance able to target intracellular proteins DNA methylation inhibitors and methods for treating cancer with DNA methylation inhibitors, as well as for treating an individual with a DNA methylation inhibitor in combination with other agents, such as a histone deacetylase inhibitor, are known in the art. Some examples are provided in U.S. Pat. No. 7,276,228 and U.S. Patent Publication Nos. 20080175814 and 20070105792. The descriptions of methylation inhibitors, histone deacetylase inhibitors, and methods of using such agents for treating cancer in an individual are incorporated herein by reference. Identification of an individual as a candidate for receiving a DNA methylation inhibitor is also considered to be an indicative that the individual is a candidate for receiving a histone deacetylase inhibitor in combination with the DNA methylation inhibitor. In one embodiment, the histone deacetylase inhibitor may be Trichostatin A (TSA).

In certain aspects, the method for treating cancer comprises administering a DNA methylation inhibitor selected from the group consisting of 5-aza-2'-deoxycytidine (5-azadc), 5-azacytidine, and combinations thereof.

In one embodiment, an inhibitor may include any suitable substance able to target intracellular proteins, small molecules, or nucleic acid molecules alone or in combination with an appropriate carrier or vehicle, including, but not limited to, an antibody or functional fragment thereof, (e.g., Fab', F(ab')2, Fab, Fv, rIgG, and scFv fragments and genetically engineered or otherwise modified forms of immunoglobulins such as intrabodies and chimeric antibodies), small molecule inhibitors of the protein, chimeric proteins or peptides, gene therapy for inhibition of transcription, or an RNA interference (RNAi)-related molecule or morpholino molecule able to inhibit gene expression and/or translation. In one embodiment the inhibitor is an RNAi-related molecule such as an siRNA or an shRNA for inhibition of translation. An RNA interference (RNAi) molecule is a small nucleic acid molecule, such as a short interfering RNA (siRNA), a double-stranded RNA (dsRNA), a micro-RNA (miRNA), or a short hairpin RNA (shRNA) molecule, that complementarily binds to a portion of a target gene or mRNA so as to provide for decreased levels of expression of the target.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. In one embodiment, the pharmaceutically acceptable carrier is a PEGylated immunoliposome for encapsulating the RNAi-related molecule. The PEGylated immunoliposomes or other carrier or delivery vehicle may be specifically targeted to breast cancer tumor cells by conjugating recombinant human and/or chimeric monoclonal antibodies or functional fragments thereof to the liposomal membrane which are specific for cell surface protein and/or carbohydrate and/or glycoprotein markers specific to the subtype that is targeted. Such markers that may be targeted include, but are not limited to, ATAD2, BRAF, DERL1, DNMTRB, NEK2A, AKT1, AURKA, AURKB, ESR2, FASN, FOXM1, TBX2, TNFRSF12A, PSENEN, HIF1A, IGF1R, MCL1, PPFIA1, RAF1, PRL, RXRA, SRD5A2, SUMO2, TYMS, UBA1, VEGFA, WNT3A, HOXA7, HOXA9, HOXA10, HOXA11, ERBB2, NEUROD2, and WNT9A.

Compositions containing pharmaceutically acceptable carriers are described in a number of sources which are well known and readily available to those skilled in the art. For example, Remington: The Science and Practice of Pharmacy (Gerbino, P. P. [2005] Philadelphia, Pa., Lippincott Williams & Wilkins, 21 st ed.) describes formulations that can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The pharmaceutical composition described above is administered and dosed in accordance with good medical practice, taking into account the clinical condition of the individual patient, the site and method of administration, scheduling of administration, patient age, sex, body weight, and other factors known to medical practitioners. The therapeutically effective amount for purposes herein is thus determined by such considerations as are known in the art. For example, an effective amount of the pharmaceutical composition is that amount necessary to provide a therapeutically effective decrease in the expression of the targeted gene. The amount of the pharmaceutical composition should be effective to achieve improvement including but not limited to total prevention and to improved survival rate or more rapid recovery, or improvement or elimination of symptoms associated with the chronic inflammatory conditions being treated and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of the patient and the route of administration.

The brain is a common site of metastatic disease in patients with breast cancer and has few therapeutic options with dismal outcomes. A deep genomic profiling was performed, which integrated gene copy number, gene expression and DNA methylation datasets on a collection of breast brain metastases. Frequent large chromosomal gains in 1q, 5p, 8q, 11q, and 20q and frequent broad level deletions involving 8p, 17p, 21p and Xq were identified. Frequently amplified and overexpressed genes included ATAD2, BRAF, DERL1, DNMTRB and NEK2A. The ATM, CRYAB and HSPB2 genes were commonly deleted and underexpressed. Knowledge mining revealed enrichment in cell cycle and G2/M transition pathways, which contained AURKA, AURKB and FOXM1. Using the PAM50 breast cancer intrinsic classifier, Luminal B, Her2+/ER negative, and basal-like tumors were identified as the most commonly represented breast cancer subtypes in our brain metastasis cohort. While overall methylation levels were increased in breast cancer brain metastasis, basal-like brain metastases were associated with significantly lower levels of methylation. Integrating DNA methylation data with gene expression revealed defects in cell migration and adhesion due to hypermethylation and downregulation of PENK, EDN3, and ITGAM. Hypomethylation and upregulation of KRT8 likely affects adhesion and permeability. Genomic and epigenomic profiling of breast brain metastasis has provided insight into the somatic events underlying this disease, which have potential in forming the basis of future therapeutic strategies.

The following examples are given for purely illustrative and non-limiting purposes of the present invention.

EXAMPLES

Example 1. Experimental Materials and Methods

The materials and methods used in the following examples are as previously described (32). These experimental materials and methods are summarized below.

Sample Acquisition

Retrospective fresh-frozen samples of breast brain metastases (BBM) were obtained. Non-neoplastic brain samples were also obtained. Ten non-neoplastic breast tissue specimens were purchased from Asterand (Detroit, Mich.). A series of 50 early-stage (grade 1 and 2) breast cancer specimens were obtained. All samples were obtained under appropriate ethical procedures and informed patient consent.

All human biospecimens used in this study were pre-existing and de-identified before genomic analysis. Investigators did not have access to patient identifiers at any time before or after completion of the study. Investigators and the holder of patient identifiers entered into an agreement prohibiting the release of this information to investigators under any circumstances. Therefore, the biospecimens do not qualify as human subjects and the study is exempt from Institutional Review Board, in accordance with the Office of Human Research Protections (OHRPs) Guidance on Research Involving Coded Private Information or Biological Specimens.

gDNA and RNA Isolation

Genomic DNA (gDNA) was isolated from fresh-frozen tissue using the DNeasy Blood and Tissue Kit (Qiagen, Valencia, Calif.) with the following modifications. Approximately 25 mg frozen tissue was pulverized after a brief incubation in liquid nitrogen, then lysed in 180 µL ATL buffer. The sample was further disrupted using a hand-held tissue homogenizer (VWR, Radnor, Pa.) before adding 204, proteinase K solution. Lysates were incubated at 56° C. for 72 hours. Following proteinase K treatment, lysates were centrifuged at 17,000×g to pellet particulate material. Genomic DNA was eluted in 100 µL T low E buffer (Teknova, Hollister, Calif.) and stored at 4° C. Total RNA, including small RNA, was isolated using the mirVana miRNA Isolation Kit (Ambion, Austin, Tex.) following the manufacturer's protocol. Genomic DNA and total RNA yields and purity were assessed using a NanoDrop 2000c (Thermo Scientific, Waltham, Mass.). Genomic DNA integrity was confirmed by agarose gel electrophoresis. Total RNA samples were evaluated for integrity using the Bioanalyzer RNA 6000 Nano LabChip Kit (Agilent Technologies, Santa Clara, Calif.) on a Bioanalyzer 2400 (Agilent Technologies). Only total RNA samples with RNA integrity number values of at least 7 (RIN≥7) were profiled. A total of 10 samples were dropped due to RIN values lower than 7.

Copy Number Analysis

Array-based comparative genomic hybridization (aCGH) was performed on 19 BBM samples using the Agilent SurePrint G3 Human CGH Microarray Kit, 1×1M, which have an average probe spacing of 2.1 Kb (Agilent Technologies). Briefly, 800 ng of experimental and normal female reference (Promega, Madison, Wis.) gDNA were independently digested with Bovine DNAse I (Ambion) and directly labeled with Cy5 and Cy3, respectively, using the BioPrime Array CGH Genomic Labeling Module (Invitrogen, Carlsbad, Calif.). Labeled DNA was purified using Vivaspin 500 columns (Satorius Stedim Biotech, Goettingen, Germany). Equal amounts of labeled, purified experimental and reference DNA were hybridized to the microarray in a rotary oven at 65° C. for 40 hr at a rotation speed of 20 rpm. The slides were washed according to manufacturer's protocol and images were captured using an Agilent DNA microarray scanner set at default settings for array-based comparative genomic hybridization. Scanner images were extracted using Feature Extraction software v. 10.5.1.1 (Agilent Technologies). $Log_2$ data was imported into Agilent DNA Analytics 4.0.81 software for visualization and quality assessment. The aCGH data for 15 of 19 BBM samples, which passed quality control metrics, were segmented using the circular binary segmentation (CBS) algorithm[6,7]. Genomic Identification of Significant Targets in Cancer (GISTIC) was then used to identify regions of the genome that were significantly amplified or deleted across the 15 breast brain metastasis samples. GISTIC calculated a statistic (G score) for the frequency of occurrence and the amplitude of the aberration. The statistical significance of each aberration was computed by comparing the observed G score to the results expected by chance. Regions with false-discovery rate (FDR) q-values less than 0.25 were considered statistically significant. In addition, copy number variation analysis was performed using Agilent's Genomics Workbench 6.5 software. The Aberration Detection Method 2 (ADM-2) algorithm was used to flag altered chromosomal regions and breakpoints (ADM-2 threshold of 5.5 within a 5.0 Mb window size containing at least 3 probes and with minimum 0.58 absolute average log ratio for the region).

mRNA Expression Profiling

RNA from 35 BBM, 10 non-neoplastic brain (NBn) and 10 non-neoplastic breast (NBr) tissue were profiled using Agilent whole human genome 4×44K mRNA expression microarrays. A quick-amplification kit (Agilent Technologies) was used to amplify and label 500 ng target mRNA species into complementary RNA (cRNA) for oligo microarrays according to the manufacturer's protocol. For each two-color array, a commercial universal reference RNA (Stratagene, La Jolla, Calif.) was labeled with cyanine 5-CTP and cyanine-3-CTP (Perkin Elmer, Boston, Mass.). Complimentary RNA concentration and labeling efficiency were measured spectrophotometrically. Approximately 800 ng of both Cy5-labeled experimental cRNA and Cy3-labeled universal reference RNA were hybridized to each microarray (adjusting for labeling efficiency). Images were captured using an Agilent DNA microarray scanner set at default settings for gene expression. Scanned images were processed using Feature Extractor v. 10.5.1.1. software by applying a LOWESS (locally weighted linear regression) correction for dye bias, background noise was subtracted from spot intensities. To filter the preprocessed data, genes with a background signal higher than feature signal were removed.

Intrinsic Subtype Classification of Breast Brain Metastasis

The PAM50 gene expression classifier is a supervised, centroid-based prediction method to classify breast cancers into intrinsic molecular subtypes (Luminal A, Luminal B, HER2-enriched, basal-like, and normal-like) using a 50-gene signature. We applied this classifier to samples analyzed on the Agilent 4×44K mRNA expression platform. Normal samples were used as controls. The log ratio values of the probes were collapsed to gene level by taking the median of all probes matching to same gene.

DNA Methylation Analysis

A total of 1 µg of DNA from 32 BBM, 12 NBr, 15 NBn samples and 48 early stage primary breast cancer samples was bisulfite converted with the EZ DNA methylation kit (Zymo Research, Irvine, Calif.) and subsequently processed for hybridization onto the Infinium HumanMethylation27 BeadArray (Illumina, San Diego, Calif.) according to manufacturers' protocols. This array interrogates 27,578 CpG dinucleotides encompassing 14,495 genes. Bisulfite-treated DNA was subsequently amplified, fragmented and hybridized to locus-specific oligonucleotides on the BeadArray. Image processing and intensity data extraction were performed using an Illumina BeadArray Reader. The GenomeStudio Methylation software from Illumina was used for data assembly and acquisition. Methylated (M) and unmethylated (U) alleles were detected by fluorescence signal from single-nucleotide extension of the DNA fragments. Results were interpreted as a methylation ratio (β value) of methylated signal (M) to the sum of methylated and unmethylated signal (M+U) for each locus. The average β-value reports a methylation signal ranging from 0 to 1 spanning completely unmethylated to completely methylated, respectively. A differentially methylated locus was defined by having a statistically significant (p-value ≤0.05 after computing a Mann Whitney non-parametric test) average β difference of at least |0.2| between groups.

Data Deposition in Public Portals

The raw Agilent gene expression array data discussed in this publication have been deposited in NCBI's Gene Expression Omnibus and are accessible through GEO Series accession number GSE52604. The aCGH and DNA methylation data are available online.

Pathway Analysis

Gene lists of interest were uploaded into IPA (Ingenuity® Systems) and the Core Analysis workflow was run with default parameters. The Core Analysis provides an assessment of significantly altered pathways, molecular networks and biological processes represented in the samples' gene list.

Quantitative Reverse-Transcriptase (RT)-PCR and Copy Number PCR Assays

Complimentary DNA (cDNA) was synthesized using 100 ng of total RNA in a 20 μl reaction volume. The Superscript® III First Strand synthesis system (Life Technologies, Carlsbad, Calif.) was used with the following conditions: 10 minutes at 25° C., 30 minutes at 50° C., 5 minutes at 85° C. and 20 minutes at 37° C. with RNase H. SYBR green fluorescence was used for the detection of amplification after each cycle using the LightCycler 480 SYBR Green I Mastermix (Roche Applied Science, Indianapolis, Ind.). Quantitative PCR (qPCR) was subsequently performed on cDNA in a final volume of 25 μl using the LightCycler 480 instrument (Roche Applied Science). The qPCR cycling conditions were as follows: 5 minutes at 95° C. for activation of Platinum® Taq DNA polymerase, 10 seconds at 95° C., 20 seconds at 59° C., and 30 seconds at 72° C. for 45 cycles. Quantification was based on the number of cycles necessary to produce a detectable amount of product above background. The following primer pairs were used.

AURKB:
(SEQ ID NO: 1)
Forward-5'-ATT GCT GAC TTC GGC TGG T-3'

(SEQ ID NO: 2)
Reverse: 5'-GTC CAG GGT GCC ACA CAT-3'

FOXM1:
(SEQ ID NO: 3)
Forward: 5'-TGG CGA TCT GCG AGA TTT-3'

(SEQ ID NO: 4)
Reverse: 5'-CCT CCT CAG CTA GCA GCA CT-3'

ATAD2:
(SEQ ID NO: 5)
Forward: 5'-CCTGCAAGACCAAGATACCG-3'

(SEQ ID NO: 6)
Reverse: 5'-TTTCCTCCGCCTCTCAAAGT-3' cMYC:
(SEQ ID NO: 7)
Forward: 5'-CTTCTCTCCGTCCTCGGATTCT-3'

(SEQ ID NO: 8)
Reverse: 5'-GAAGGTGATCCAGACTCTGACCTT-3'
The β-actin, Histone and GAPDH genes were used as an internal reference controls.

Histone:
(SEQ ID NO: 9)
Forward: 5'-CCACTGAACTTCTGATTCGC-3'

(SEQ ID NO: 10)
Reverse: 5'-GCGTGCTAGCTGGATGTCTT-3'

GAPDH:
(SEQ ID NO: 11)
Forward: 5'-CTGCACCACCAACTGCTTAG-3'

(SEQ ID NO: 12)
Reverse: 5'-GTCTTCTGGGTGGCAGTGAT-3'

For each sample, the delta Ct value was calculated as the difference between the target gene Ct value and the Ct value of the geometric mean of the internal reference controls. The quantity of expression was calculated relative to the average of expression obtained from NBr and NBn samples (n=6). The equation used for relative fold-change was $2^{-\Delta\Delta C_T}$.

Copy number validation was completed with the qBiomarker Copy Number PCR Assays (Qiagen, Valencia, Calif.) for ATAD2 (Assay ID 28855976), and cMYC (Assay ID 28877687). Samples were analyzed with the qBiomarker SYBR ROX Mastermix (Qiagen). A multi-copy reference assay, the qBiomarker Multicopy Reference Copy Number PCR Assay (MRef, Assay ID 30773761) was performed for each sample and served as the internal reference control. Data were analyzed with qBiomarker Copy Number PCR Assay Data Analysis Software.

All PCR reactions were run in triplicate, and melting curve analysis was performed to ensure specificity of the PCR product. Negative (no template) controls were run in parallel to confirm the absence of nonspecific fluorescence in samples.

Example 2. Copy Number Analysis

Somatic copy number analysis (SCNAs) was conducted using the one-million feature aCGH platform in 15 breast brain metastases genomes to identify regions of gain or loss. GISTIC analysis identified 18 focal amplifications (FIG. 1) and 4 regions of broad amplifications involving 1q, 5p, 8q, 11q, and 20q (FIG. 1). Among the genes amplified in the focal regions were a cluster of HOX genes (HOXA7, HOXA9, HOXA10, HOXA11) on 7p15, AKT1 (14q32.33), IGF1R (15q26.3), ERBB2 and NEUROD2 (17q12), all of which have been reported in primary breast cancers. GISTIC also identified 37 focal deletions involving CDKN2A, CDKN2B, and DMRTA1 (FIG. 1). Four regions of broad deletions included 8p, 17p, 21p and Xq (FIG. 1).

Example 3. mRNA Expression Analysis

Figure 2:
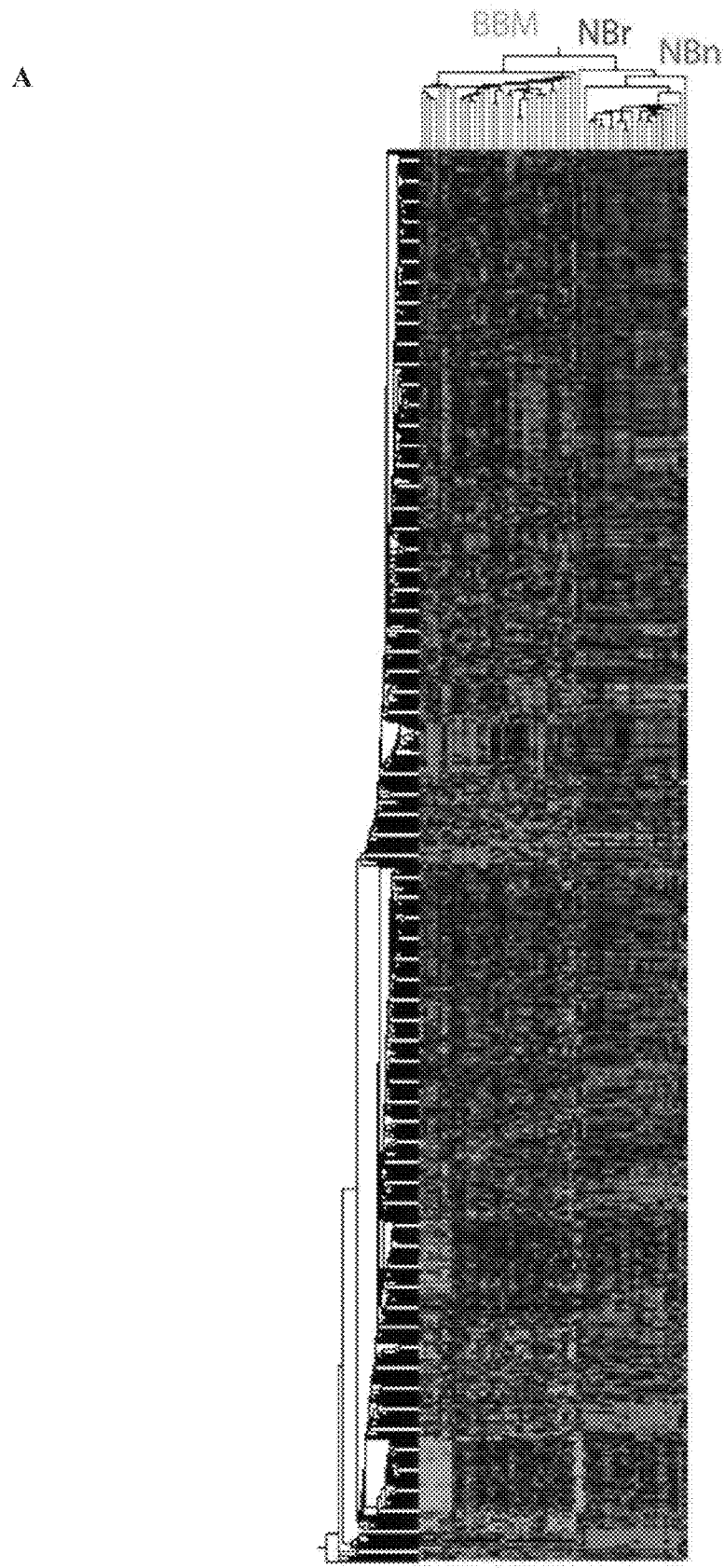
FIGS. 2A-2E depict an analysis of differentially expressed genes in breast brain metastasis.
Figure 2B:
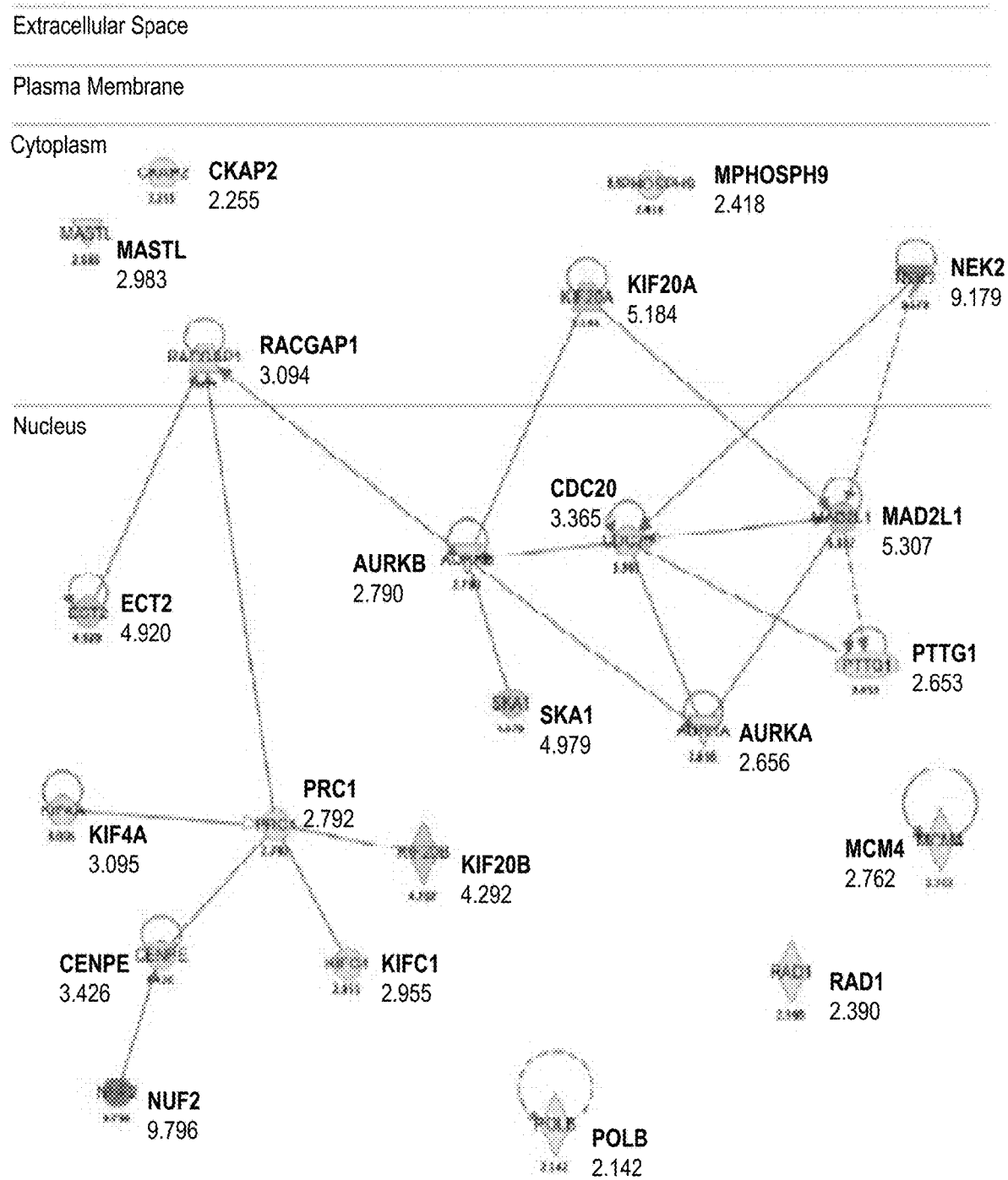
Figure 2C:
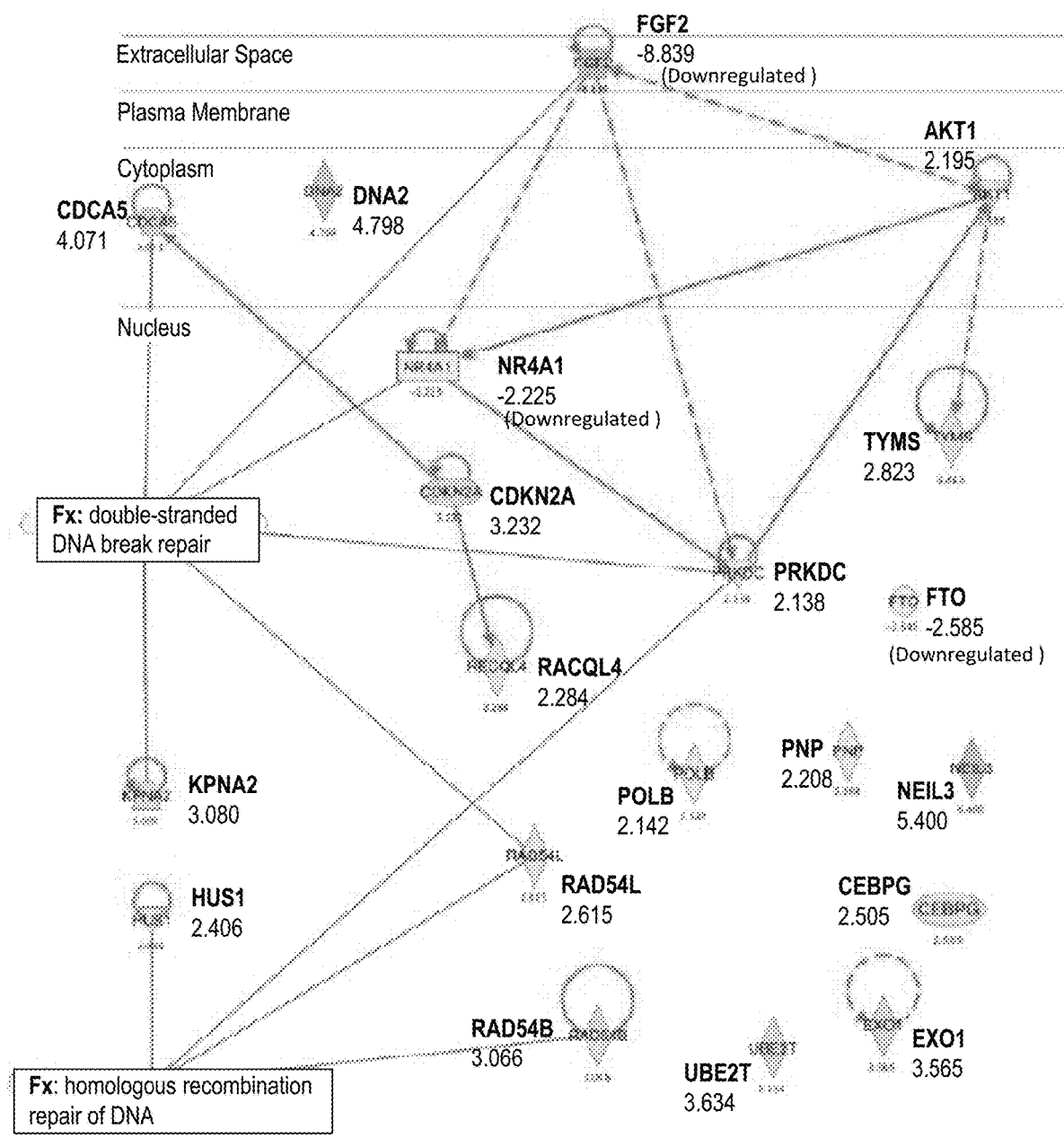

Gene expression profiling was performed using Agilent whole human genome 4×44K mRNA expression microarrays to identify differentially expressed genes (DEG) BBM samples and an independent set of nonmalignant hyperplastic breast samples (NBr) and nonmalignant brain samples (NBn). DEG were selected if differential expression was evident between tumor samples and NBn; between tumor samples and NBr but not between NBn and NBr. In addition, DEG were selected based on p-values ≤0.05 and a fold-change ≥2 or ≤−2. This comparison identified 863 differentially expressed genes. A heatmap was generated in Genespring V12.1 to visualize the DEG list, which also showed a clear separation of tumor and non-neoplastic samples (FIG. 2A). In order to identify biological concepts altered in the differentially regulated BBM gene list we submitted the gene list to IPA (Ingenuity® Systems) and applied the Core Analysis workflow. The functional analysis portion of the workflow identified biological functions and/or diseases most significantly altered in our DEG list. Significant categories were sorted based on activation/inhibition z-scores to identify the most significant distinguishing categories with respect to up-regulated and down-regulated genes. Fourteen specific functions had increased activation states as evidenced by z-scores ≥2. Five of the fourteen functional annotations mapped to the 'Cell Cycle' category. The genes defining the five categories and their relationships were visualized as a network in (FIG. 2B). 'DNA repair' was another noteworthy enriched category. The genes that mapped to this category were also visualized as a network (FIG. 2C). Enrichment analysis was performed to annotate further the genes in this category. Two DNA repair processes, double-stranded DNA break repair (CDCA5, FGF2, NR4A1, PRKDC, RAD54L, KPNA2) and homologous recombination repair (HUS1, PRKDC, RAD54L and RAD54B) were identified and highlighted in FIG. 2C. The functional annotation categories for downregulated genes converged mostly on categories associated with 'tissue morphology' and 'development'.

To identify potential transcriptional regulators among the differentially expressed genes we used the results of the upstream regulator analysis. This part of the core analysis workflow connects transcriptional regulators in the IPA database to the differentially expressed genes. Overconnected regulators are scored with a p-value, for gene enrichment, and z-score for degree of activation based on direction of regulation in database and concordance with direction of regulation in DEG. The list of upstream regulators was filtered for 'transcription regulators' upregulated (z-score ≥2) and downregulated (z-score ≤2). Five specific transcription factors were identified as active and six were identified as inhibited. One of the inhibited transcription factors was TP53, implying that TP53 signaling is defective in BBM. Among the activated transcription factors, IRF1 and IRF7 seemed to be connected preferentially to genes involved in immune response such as 'antiviral response' and antimicrobial response.' This may indicate a possible infiltration of immune cells in the samples or could reflect an immunogenic response by the tumor cells. Two interesting transcriptional regulators highly scored were FOXM1 and TBX2 that had three commonly regulated genes. We constructed a combined network illustrating the downstream transcriptional functional targets for both transcription factors. A functional enrichment was performed on the resultant network indicating that the these two transcription factors control the expression of genes enriched for processes such as cell cycle progression (p-value 4.1E-15), mitosis (p-value 4.97E-13) and cytokinesis (p-value 1.98E-10). This observation, coupled with the above functional enrichment on the whole gene list suggests that breast cancer brain metastasis gene expression is associated with cell cycle/mitosis and may be driven by FOXM1 and TBX2.

Figure 2D:
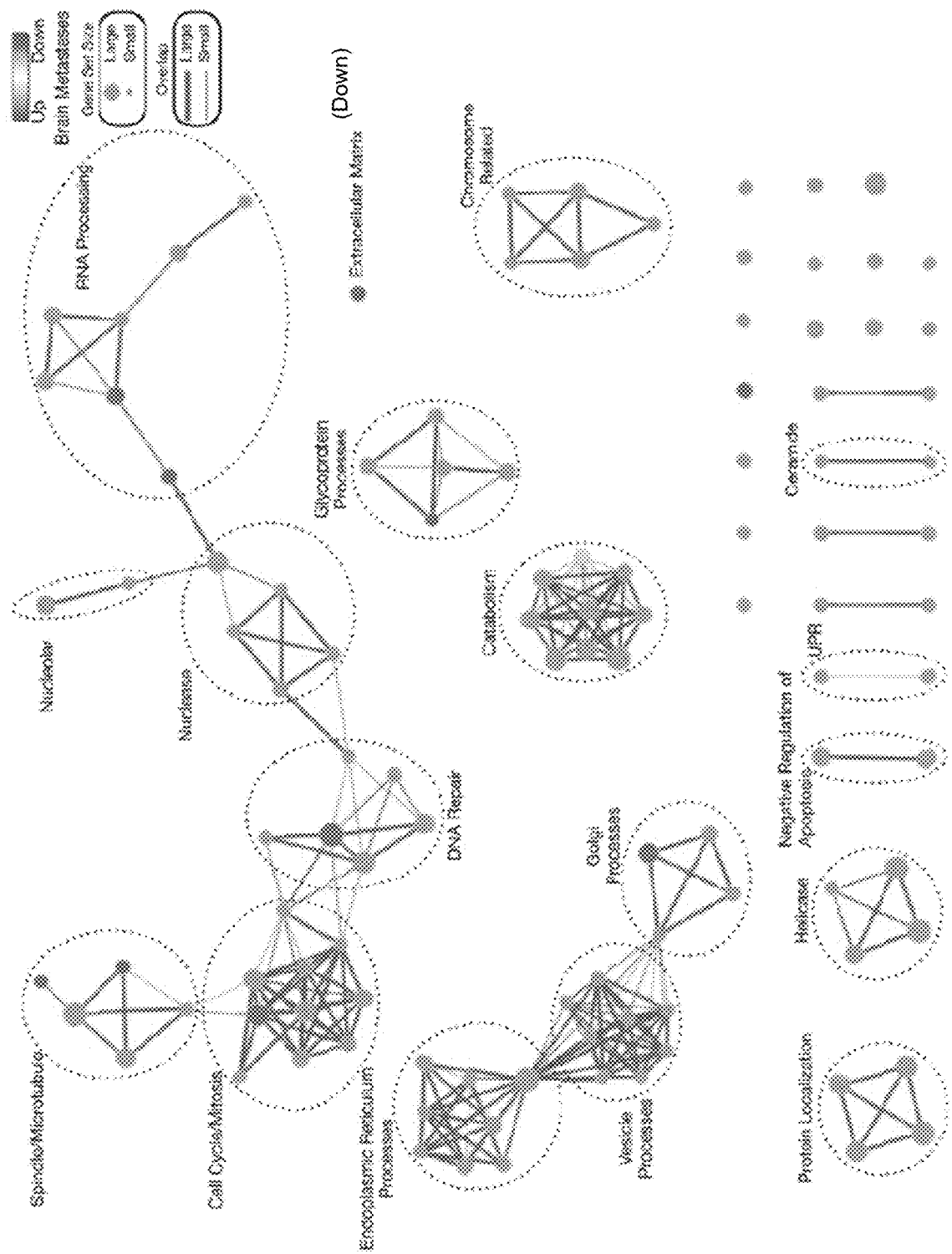
Figure 2:
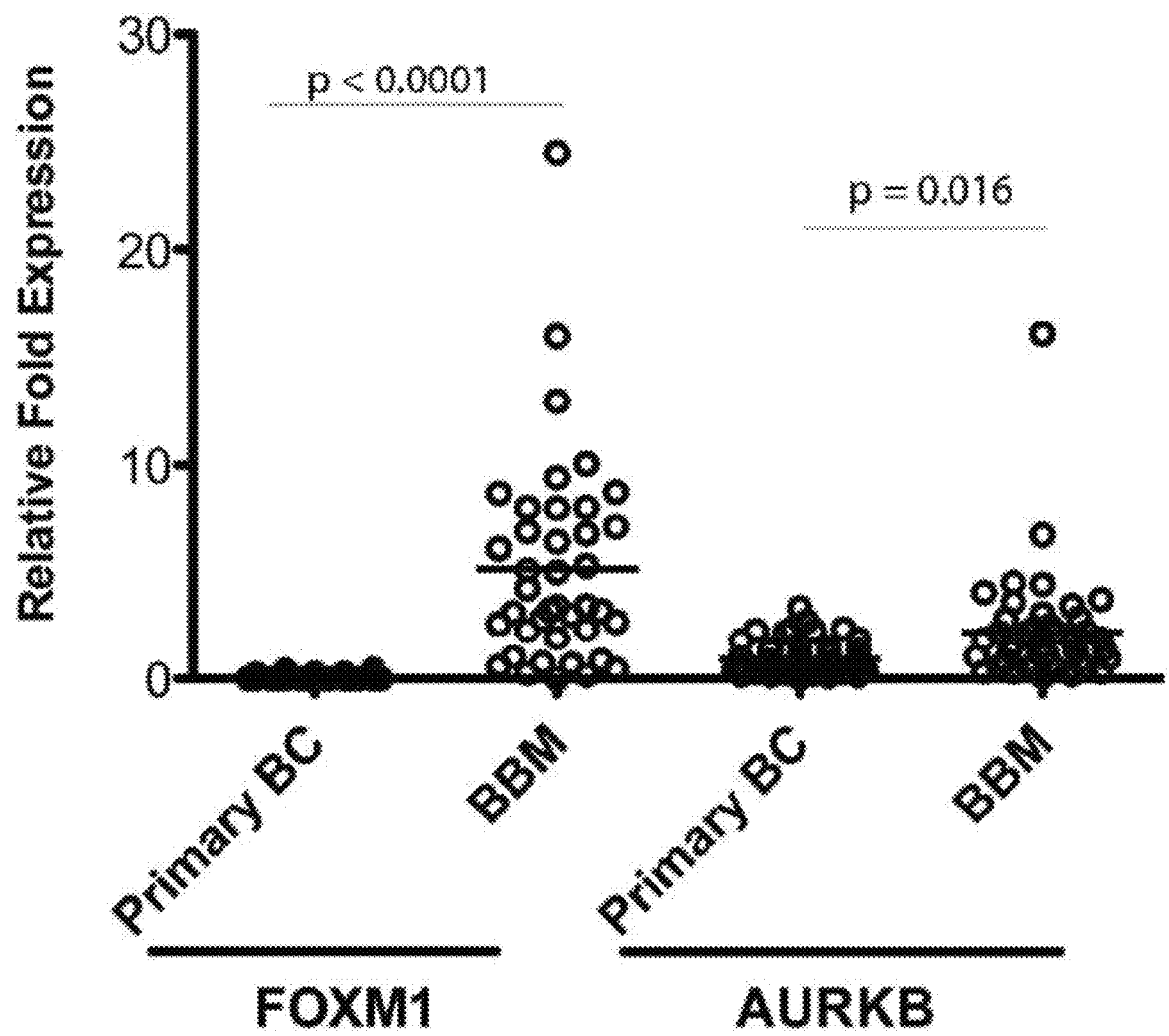

Next, we used gene set enrichment analysis (GSEA) to identify sets of genes that are coordinately regulated in the BBM samples. The GSEA algorithm identifies gene sets enriched at the top (breast brain metastases) or bottom (non-neoplastic samples) of the ranked list of differentially expressed genes. We conducted the GSEA analysis using only the c5 gene set library (GSEA|MSigDB), which contains only gene ontology gene sets. There were 109 gene sets significant at a FDR <50% and p-value of ≤0.05 that were upregulated in the breast brain metastases and only one gene set downregulated. We visualized the above referenced gene sets using the Enrichment Map plugin for cytoscape [8]. The enrichment map portrays the GSEA results as a network of gene sets (nodes) connected by edges representing overlapping genes. The enrichment map improves interpretation of GSEA results by allowing for the identification of functional groupings of the enriched gene sets. We manually inspected the resultant clusters and assigned summary labels to individual sub networks of interest. Some interesting sub networks enriched in the BBM samples include Cell Cycle/Mitosis, DNA repair, Vesicle Processes, Protein Localization and RNA processing. The only category associated with the non-neoplastic samples was extracellular matrix (FIG. 2D). We experimentally validated the expression of FOXM1 and AURKB in 42 breast brain metastasis samples (which included those used in the expression arrays) and in a series of 50 primary breast cancer samples by qRT-PCR. Both FOXM1 and AURKB were significantly upregulated in brain metastasis samples compared to primary breast cancer samples and non-neoplastic samples (FIG. 2E).

Example 4. Breast Cancer Intrinsic Subtype Analysis of Breast Brain Metastasis

Figure 3:
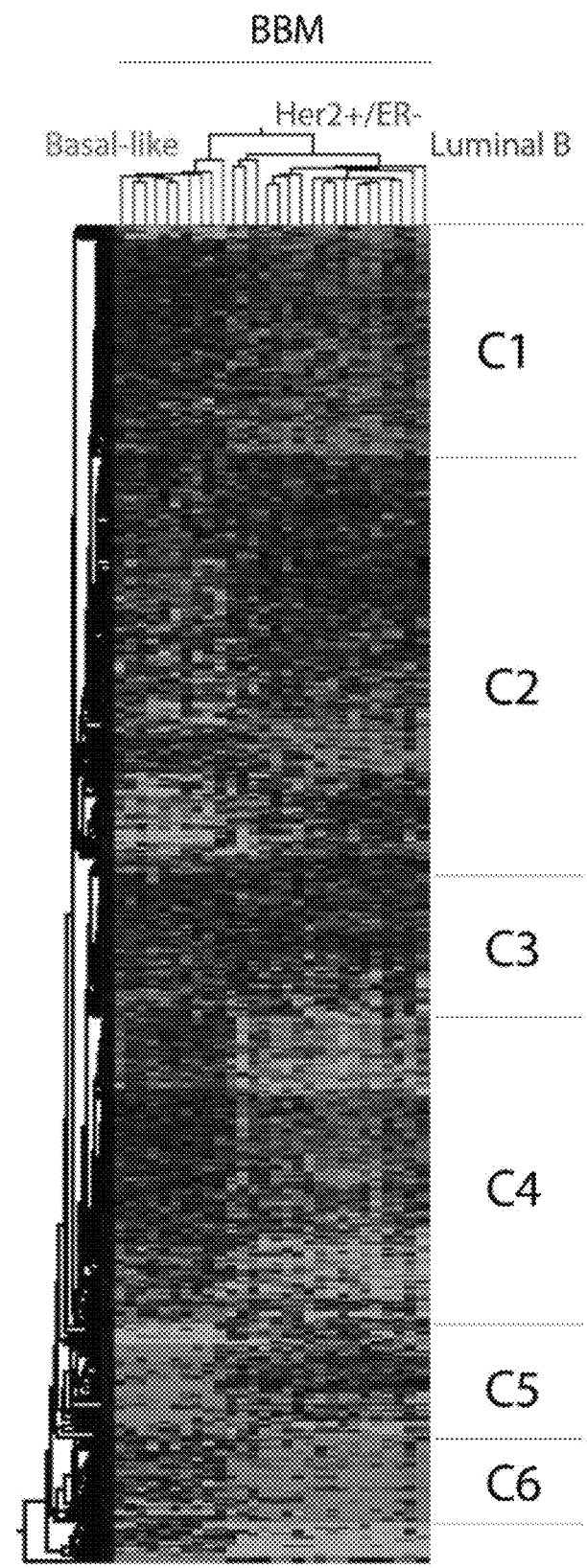
FIG. 3 depicts hierarchical clustering of genes that differentiated brain metastases based on their breast cancer intrinsic subtype status. Six distinct clusters were identified and their respective genes further analyzed.

We used the PAM50 gene expression classifier to divide the breast brain metastatic samples into the common intrinsic subtypes known for breast cancer. From this analysis we identified the following subtypes in our sample cohort: 2 (5.7%) Luminal A, 12 (34.2%) Luminal B, 8 (22.8%) Her2+/ER−, 11 (31.4%) basal-like, and 2 (5.7%) Normal-like tumors. An unsupervised clustering analysis of the 802 differentially expressed genes failed to discriminate between the different subtypes (FIG. 2A). Therefore, we performed an analysis of variance (ANOVA) to identify DEG between Luminal B, Her2+/ER− and basal-like tumors. A Post-hoc Tukey test and a Benjamin Hochberg multiple correction were applied to the data. Differences with fold-change <2 were excluded. We excluded tumors classified as Luminal A and normal-like due to a very small sample size. There were 733 DEG between Luminal B and basal-like tumors; 492 DEG between Her2+/ER− and basal-like and 223 DEG between Luminal B and Her2+/ER−. The union of the differentially expressed genes between groups consisted of 774 unique genes or 886 probe sets. Hierarchical clustering using this gene list was able to clearly distinguish the subtypes and six distinct gene clusters were identified (FIG. 3).

The genes in each cluster were analyzed using ToppGene suite and data is presented in tables and as summary word clouds for enriched processes and signatures. Cluster 1, 2 and 6 contained genes upregulated in both the Her2+/ER− and Luminal B subtypes. However, expression was generally highest in the Luminal B brain metastases. Enrichment analysis of genes in clusters 1, 2 and 6 using the ToppFun module of the ToppGene suite revealed genes previously associated with breast cancer signatures [9]. Specifically, those signatures were associated with luminal subtypes and estrogen receptor (ER)-positive breast cancer. Additionally, cluster 1 has overexpression of RET, and ERBB3, which represent possible actionable therapeutic targets. Cluster 2, similar to clusters 1 and 6, contained genes also upregulated across the Her2+/ER− and Luminal B samples. This cluster contained GATA3, which is an ESR1 target gene but was only expressed in the Luminal B tumors. Of note, in cluster 6 ESR1 was most highly expressed in Luminal B tumors, coincidentally with AR. Basal-like tumors had a negative expression value for ESR1 and AR. We also note highest expression of FLT3 and FOXA1 genes in Luminal B tumors. Expressed highly in both Her2+/ER− and Luminal tumors were the TFF3 and LRRC6. Genes in cluster 3 and 5 were, in general, preferentially upregulated in the basal-like samples. The gene lists were consistent with known basal-like breast cancer genes and are also known to be lowly expressed in Luminal breast cancer. For example, Keratin 5, 6 and 14, and CDH3 were present in cluster 5. In addition, FOXC1 and CHST3 in cluster 3 and UGT8, and CHODL genes in cluster 5 were among the highly expressed genes in basal-like tumors. Cluster 4 is unique in that it has a number of genes down regulated across the three subtypes, however, there was a more pronounced down-regulation in the Her2+/ER− and Luminal B subtypes. Interestingly, this cluster contained a number of proliferation-associated genes but they were relatively underexpressed. The basal cell marker gene, Keratin 17, is overexpressed in the basal samples across this cluster. WNT pathway members, FZD7 (C3), WNT6 (C4), WNT11 (C5) and FZD9 (4) were all preferentially expressed in basal-like tumors suggesting novel therapeutic opportunities for basal-like breast cancer brain metastases. Her2+/ER− tumors were associated with overexpression of TMEM45b, very reminiscent of a Her2 subtype. While these samples had some commonly expressed genes with the basal-like tumors, such as CLDN8, they were most similar to the Luminal B tumors. They also had the highest expression of TML5, CYP4F8, and PAX9 when compared to the other subtypes.

Example 5. DNA Methylation Analysis

Figure 4:
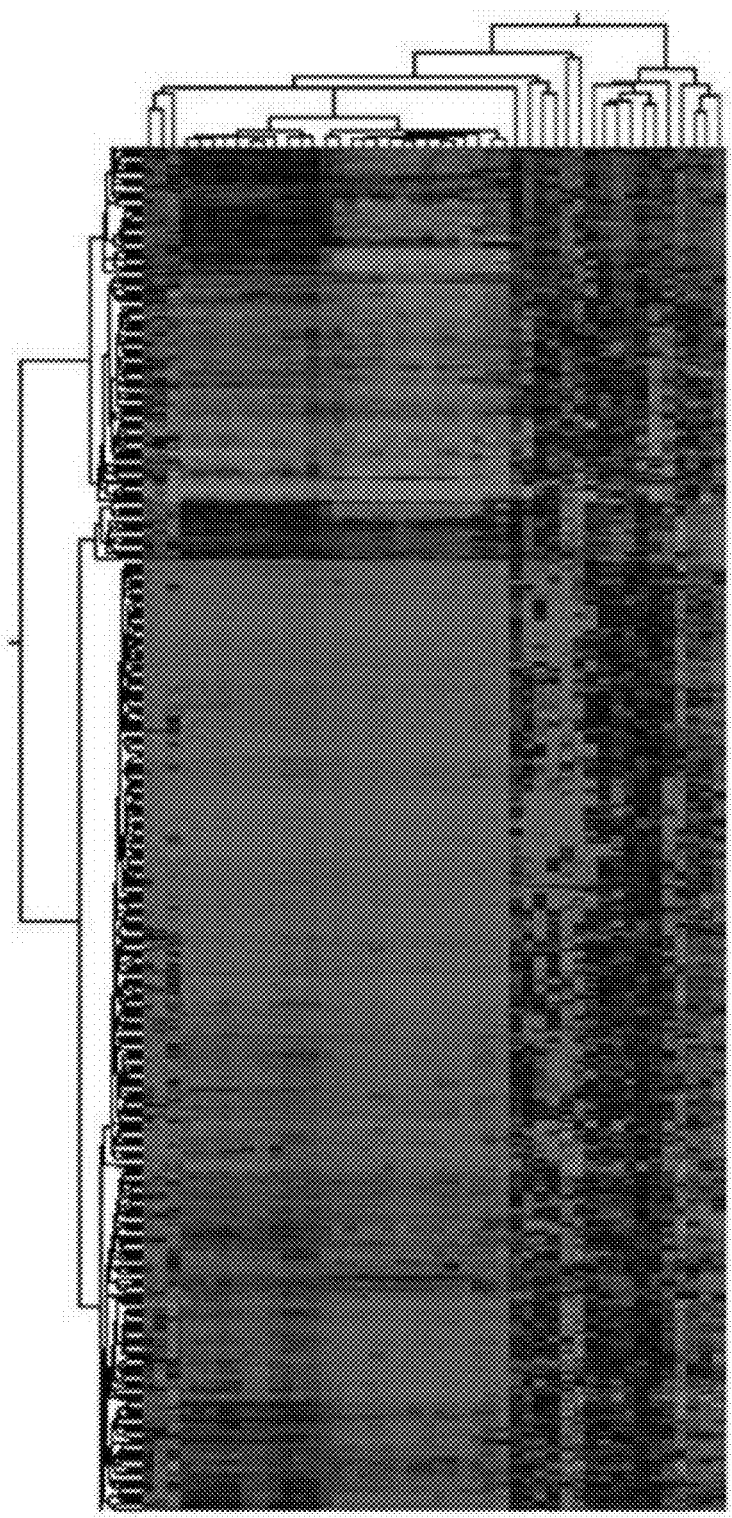
FIGS. 4A-4F depict differential methylation analysis in breast brain metastases.
Figure 4:
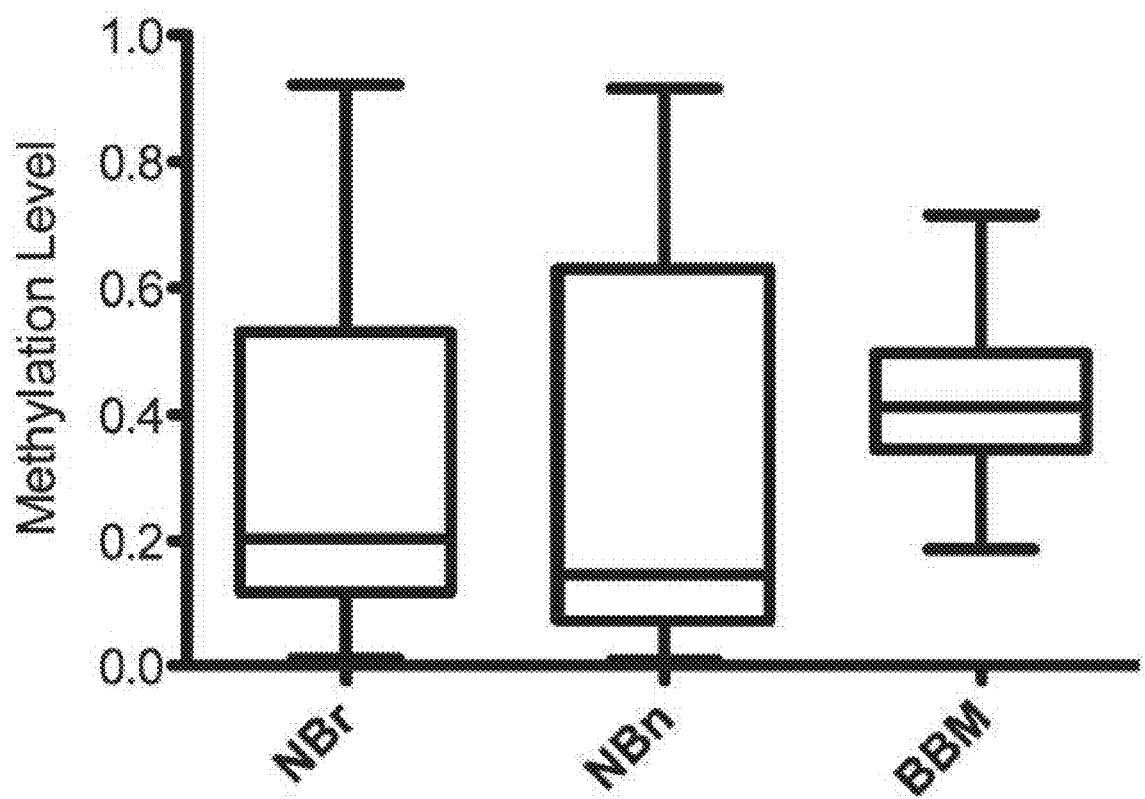
Figure 4:
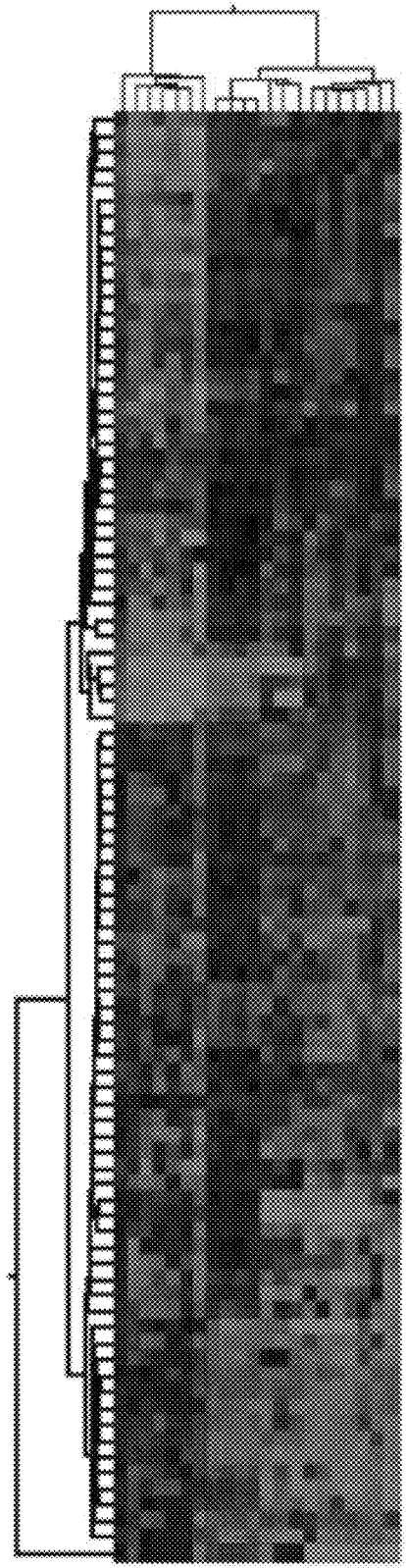
Figure 4:
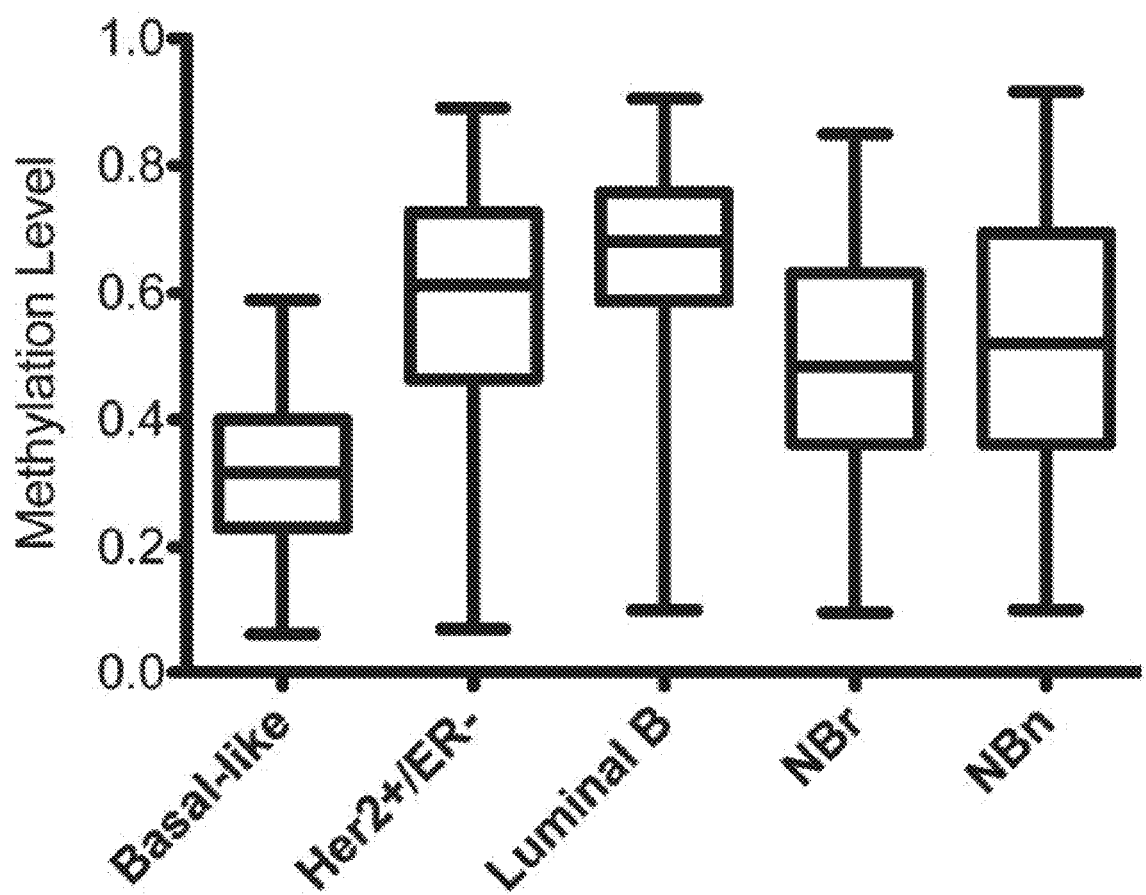
Figure 4:
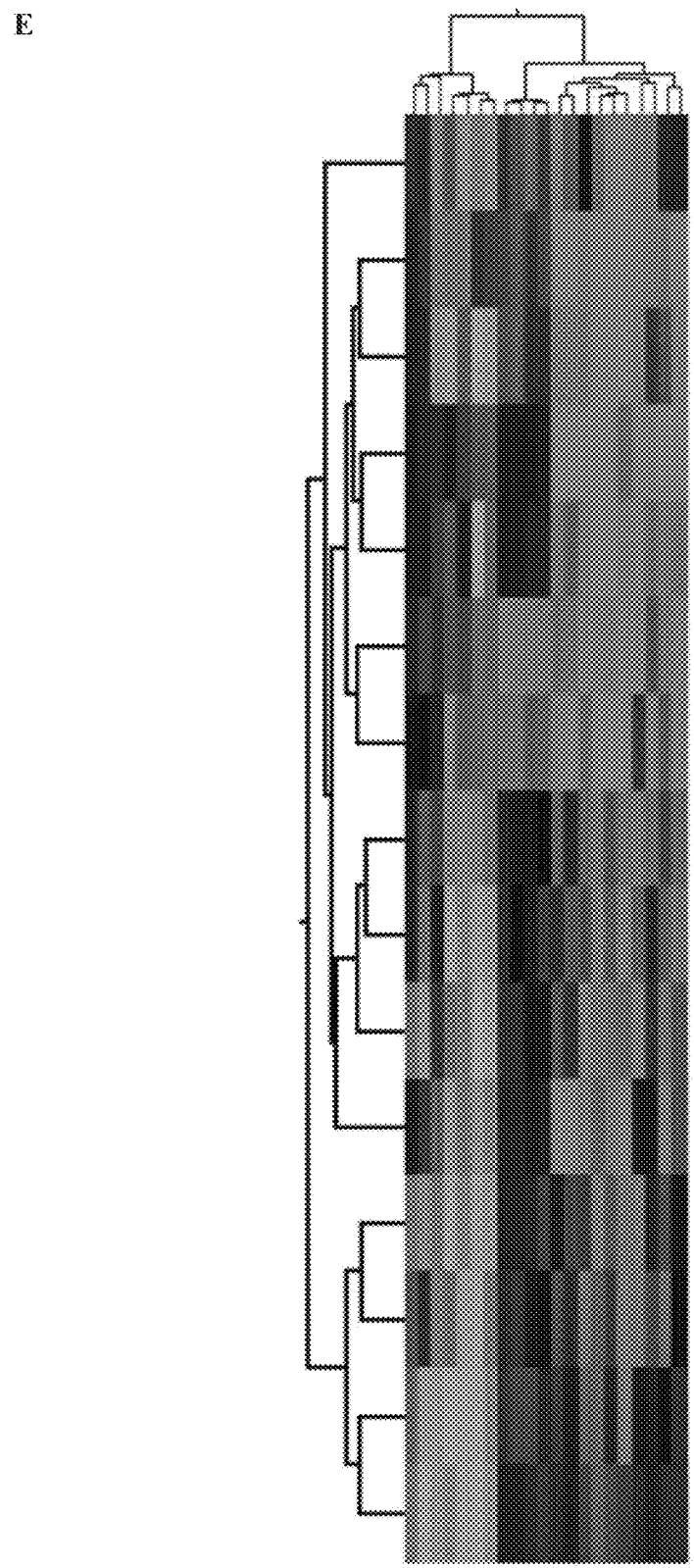
Figure 4:
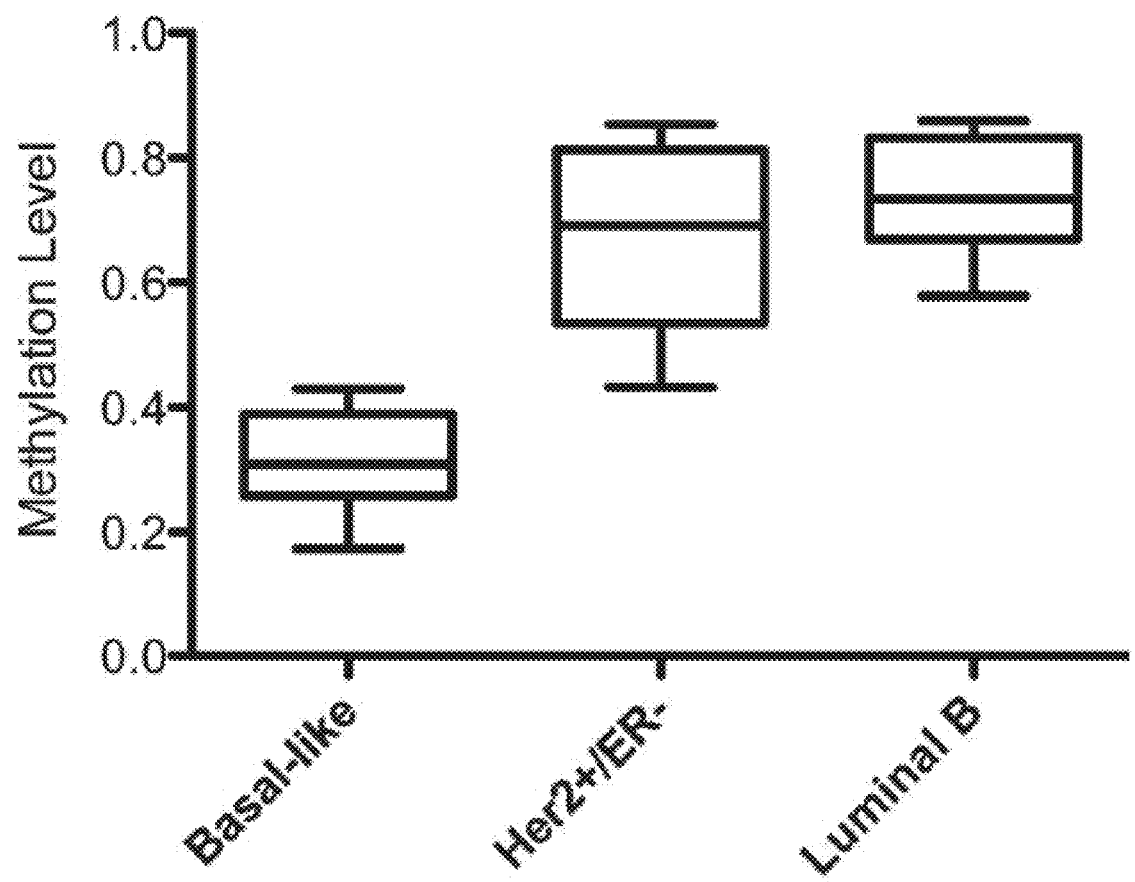

In order to identify alterations in DNA methylation we used the HumanMethylation27 BeadChip array. We compared BBM to NBn and NBr tissue and identified 425 differentially methylated loci (DML, FIG. 4A). The median methylation values were 0.4, 0.2 and 0.15 for breast brain metastasis, NBn and NBr respectively, indicating that breast brain metastasis was associated with hypermethylation (FIG. 4B). Of the 425 loci, 117 were hypomethylated compared with non-neoplastic tissue and 308 were hypermethylated. Only 23 of the hypomethylated loci were associated with CpG islands, compared to 294 hypermethylated loci, which occurred in CpG islands. The 425 DML failed to discriminate between the molecular subtypes (FIG. 4A) so we performed an ANOVA analysis to identify differentially methylated loci between the subtypes. A Post-hoc Tukey test and Benjamin Hochberg multiple correction were applied to the data. Differences with β values less than |0.2| were excluded. Due to small numbers of samples, we excluded tumors classified as Luminal A and normal-like. There were 95 DML between Luminal B and basal-like tumors; 71 DML between Her2+/ER− and basal-like tumors; and 13 DML between Luminal B and Her2+/ER−. The union of these loci resulted in 90 unique DML that discriminated between the subtypes (FIG. 4C). When the union of these loci were examined, basal-like tumors had the lowest median methylation (0.32) compared with Her2+/ER− and Luminal B subtypes (0.61 and 0.68 respectively, FIG. 4D), including non-neoplastic tissue examined. From these DML we identified a subset of 15 DML that were most hypomethylated in basal-like tumors compared to the other subtypes (FIG. 4E-F). This signature represents a potential CpG island hypomethylator phenotype (CIHMP) for basal-like breast brain metastasis and includes ALDH1A3, FANCG, TRIM29 and HOXA11.

Example 6. Combined aCGH and Gene Expression Analysis on Single Tumors

Next, we undertook a single tumor level analysis to identify a tumor specific, n=1, investigation into altered biological concepts specific to single samples. A combined copy number and gene expression based analysis was conducted on 11 individual BBM samples. In brief, the ADM2 gene level data were matched to gene level mRNA expression data. Each sample was compared against non-neoplastic tissue as described above. Genes were filtered to include only those with a $\log_2$ ratio ≥2 or ≤−2. For copy number data, a filter was applied to the ADM2 log 2 ratio to include only those genes with values ≥0.5 or ≤−0.8. The remaining data were then filtered for congruency to ensure consistency in direction of combined data, i.e. genes needed to be amplified/overexpressed or deleted/underexpressed. The combined aCGH and mRNA expression lists for each sample were uploaded into Metacore software (Thomson Reuters) for functional ontology enrichment, pathway mapping and knowledge mining. Each sample was interrogated with this workflow to identify biological concepts and observations which include single gene alterations as well as pathway-based alterations. Expert review of data was conducted to identify and prioritize important biology and concepts for each sample. Below we describe the top concepts identified in our samples.

We were able to identify at least one specific pathway/concepts aberrantly operative in each sample. There were 3 samples that had alterations, which would predict interference with the autophagy pathway. One sample had amplifications in two genes, eiF2AK3 and ATF6, which are crucial members of the endoplasmic stress pathway. Multiple alterations were observed in one sample in the WNT signaling pathway. Additionally, two samples had multiple alterations in the Chromosome Condensation pathway. Lastly, six samples had amplifications and coupled overexpression of a histone gene cluster involving the genes HF3A and HF3B.

We also note a number of interesting genes (number of samples in parentheses) that were amplified and overexpressed: AKT1 (2), ATAD2 (7), AURKA (2), BRAF (3), DERL1 (6), DNMTRB (3), ESR2 (1), FASN (3), TNFRSF12A (2), PSENEN (4), HIF1A (2), IGF1R (1), NEK2A (6), MCL1 (1), PPFIA1 (1), RAF1 (2), PRL (1), RXRA (1), SRD5A2 (1), SUMO2 (1), TYMS (2), UBA1 (1), VEGFA (1), WNT3A (2) and WNT9A (2). Genes of interest (and number of samples) that were deleted and underexpressed were: CTNNA3 (2), ATM (4), TCF4 (1), CDKN2A (1), CDKN2B (2), MSH6 (1), RB1 (1) and RPS6KA3 (2), CRYAB (4), HSPB2 (4).

Figure 5:
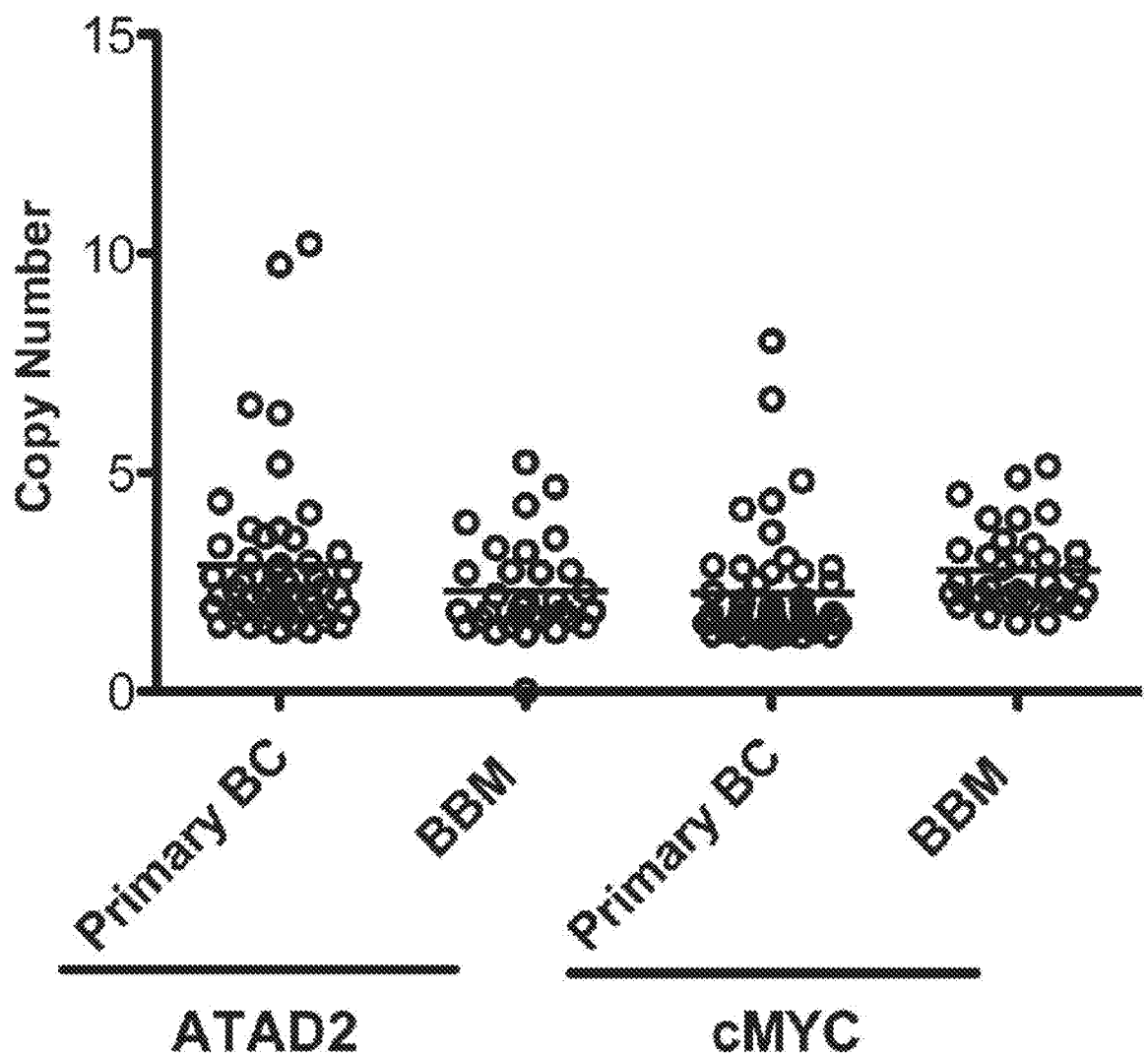
FIG. 5 depicts validation of ATAD2 and cMYC copy number and gene expression in breast brain metastasis (BBM, n=42) and early stage primary breast cancer samples (n=50). A) Vertical scatter plots demonstrate a copy number gain of ATAD2 and cMYC by qPCR but with no difference between BBM and primary breast tumors. B) Vertical scatter plots show comparative overexpression of ATAD2 in both primary tumors and primary breast cancer, whereas cMYC is not expressed. None of the comparisons between primary tumors and BBM samples were statistically significant (p>0.05).
Figure 5:
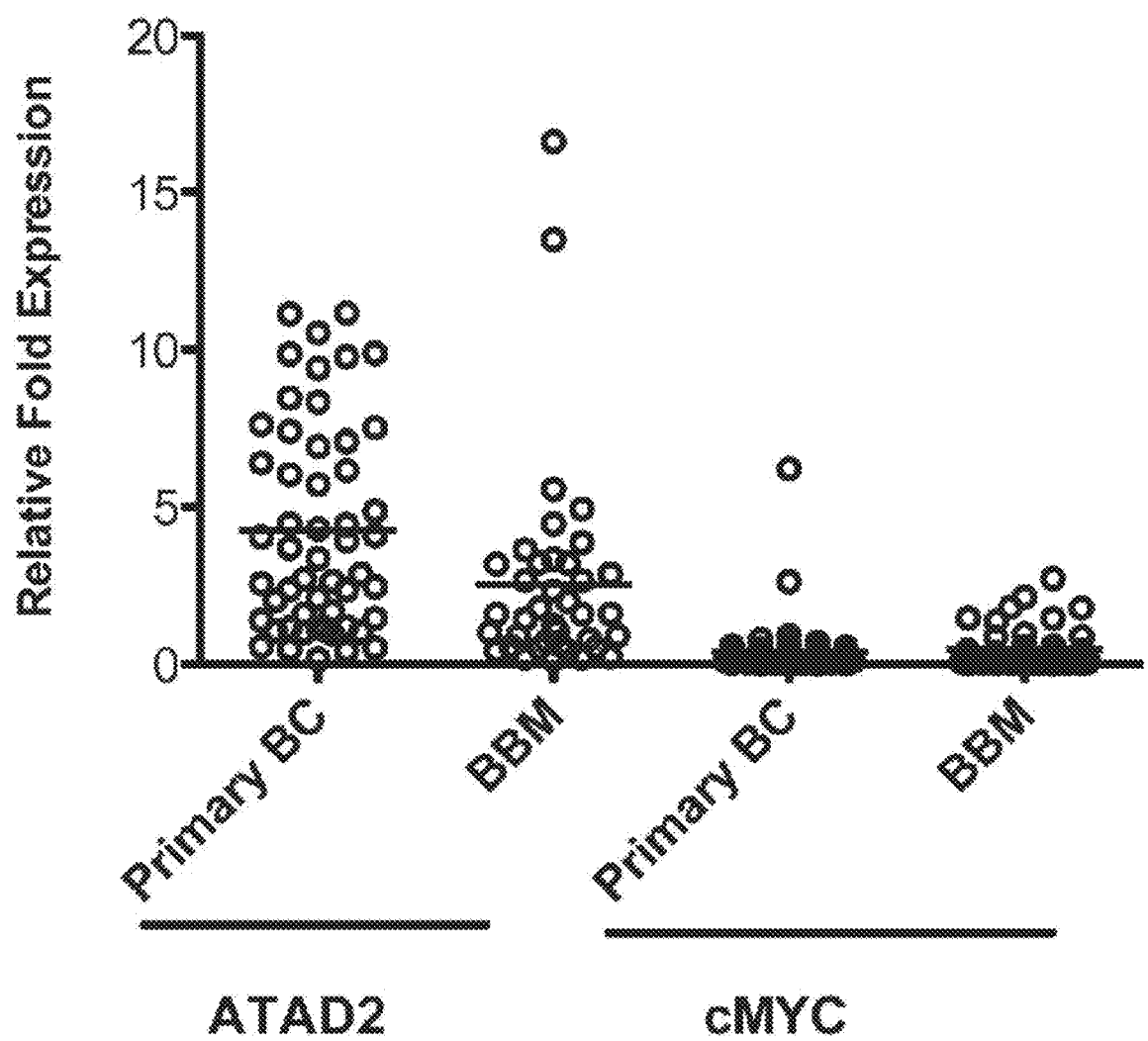

We selected the ATAD2 gene for copy number and gene expression validation by qRT-PCR and copy number qPCR assays due to its high frequency of alteration shown by aCGH and gene expression arrays. In addition, its position on 8q24, a known hotspot locus in breast cancer, further suggests the potential importance of this gene. Here we examined 42 breast brain metastases and 50 primary breast cancer samples. The BBM samples included all samples analyzed by aCGH and the gene expression array platform as well as additional samples. These data demonstrated that both metastatic and primary samples had a comparable increase in both copy number and expression of ATAD2 compared to non-neoplastic samples (FIG. 5). The cMYC gene, which is also positioned on 8q24, demonstrated gene amplification in 10/15 samples by aCGH but was not accompanied by an increase in gene expression. QPCR for copy number determination in conjunction with qRT-PCR for expression analysis yielded similar findings where there was a noticeable but similar cMYC amplification in both brain metastasis and primary breast cancer samples without any evidence of gene expression (FIG. 5)

Figure 6:
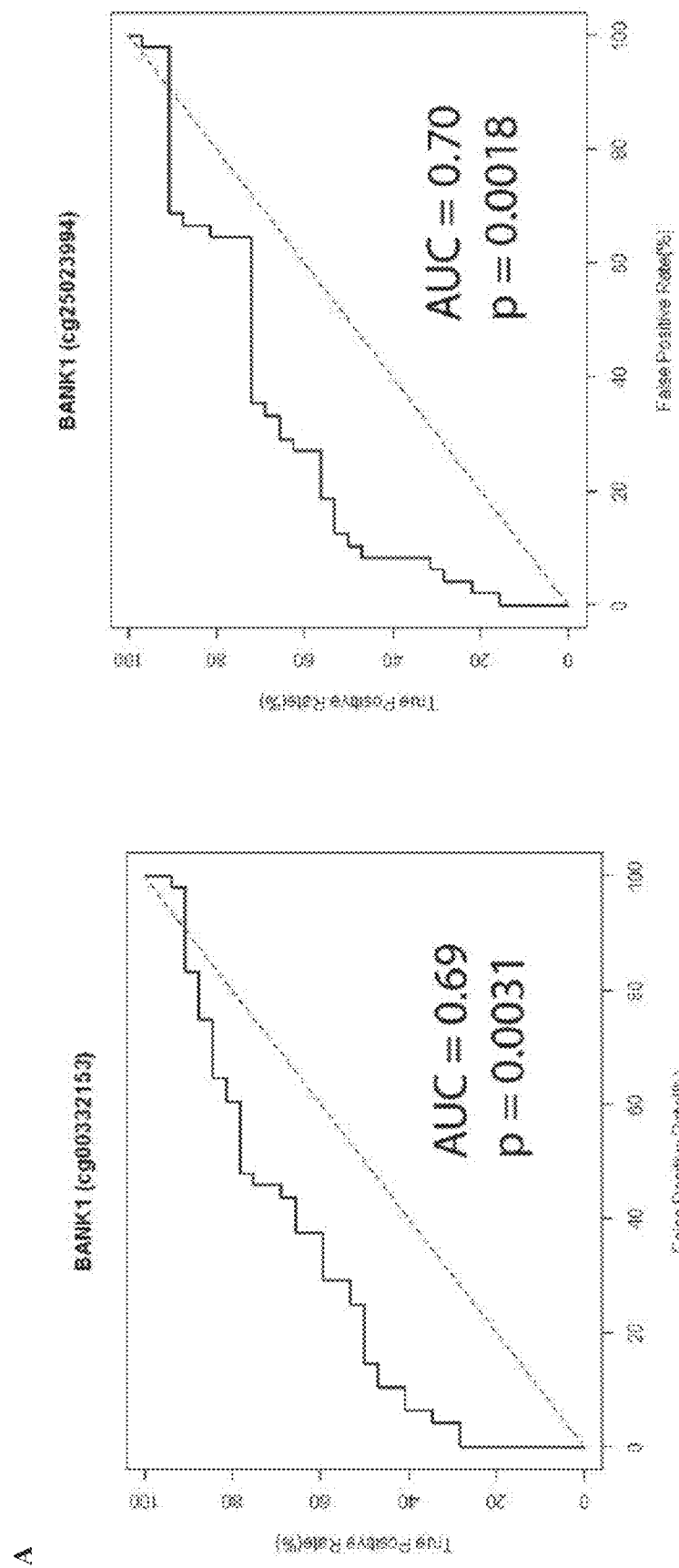
FIG. 6 depicts receiver operator characteristic (ROC) curve for A) BANK1 and B) CDKN1C for determining differential DNA methylation between BBM (n=32) and primary breast tumors (n=48). The ROC curve is a graph of the true positive rate versus the false positive rate using different threshold values. Data plotted represent two BANK1 HumanMethylation27 array probes and 6/8 CDKN1C probes that demonstrated statistically significant differential methylation between BBM and primary tumors. The area under the curve (AUC) and p vales are indicated on the graphs.
Figure 6:
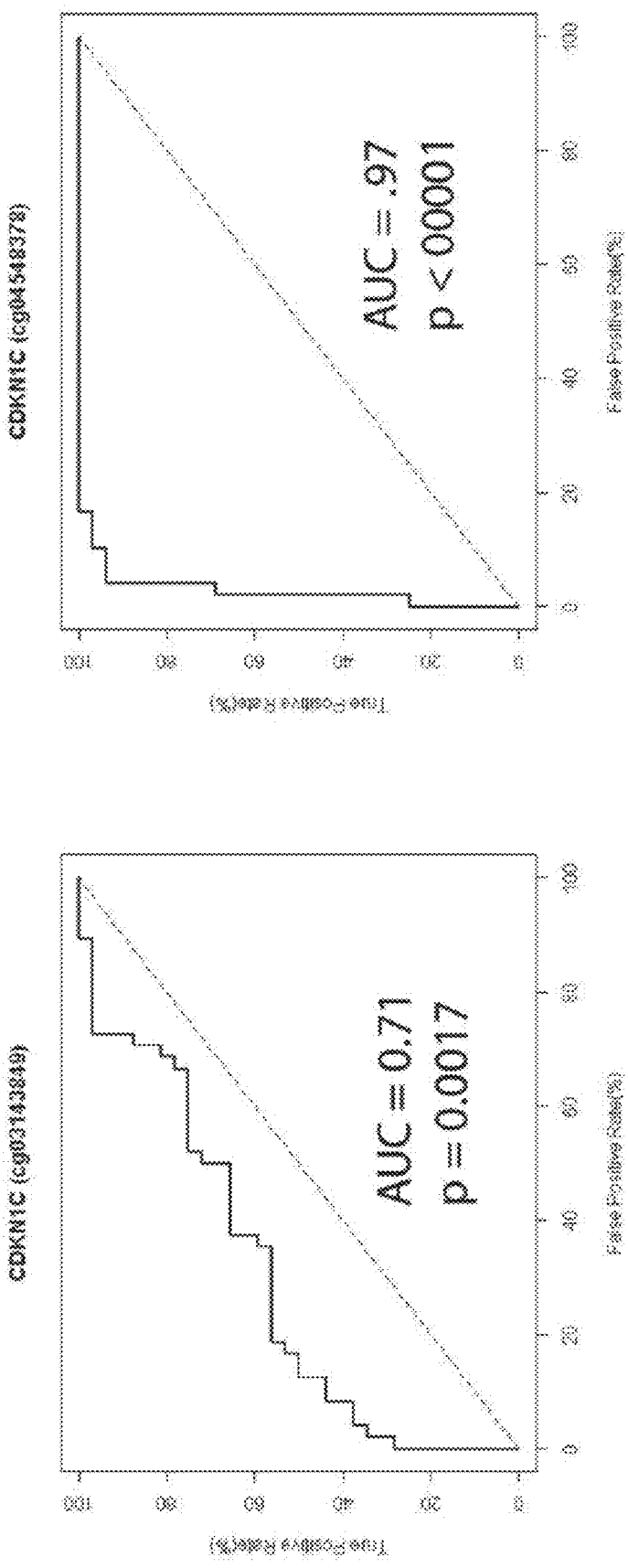
Figure 6:
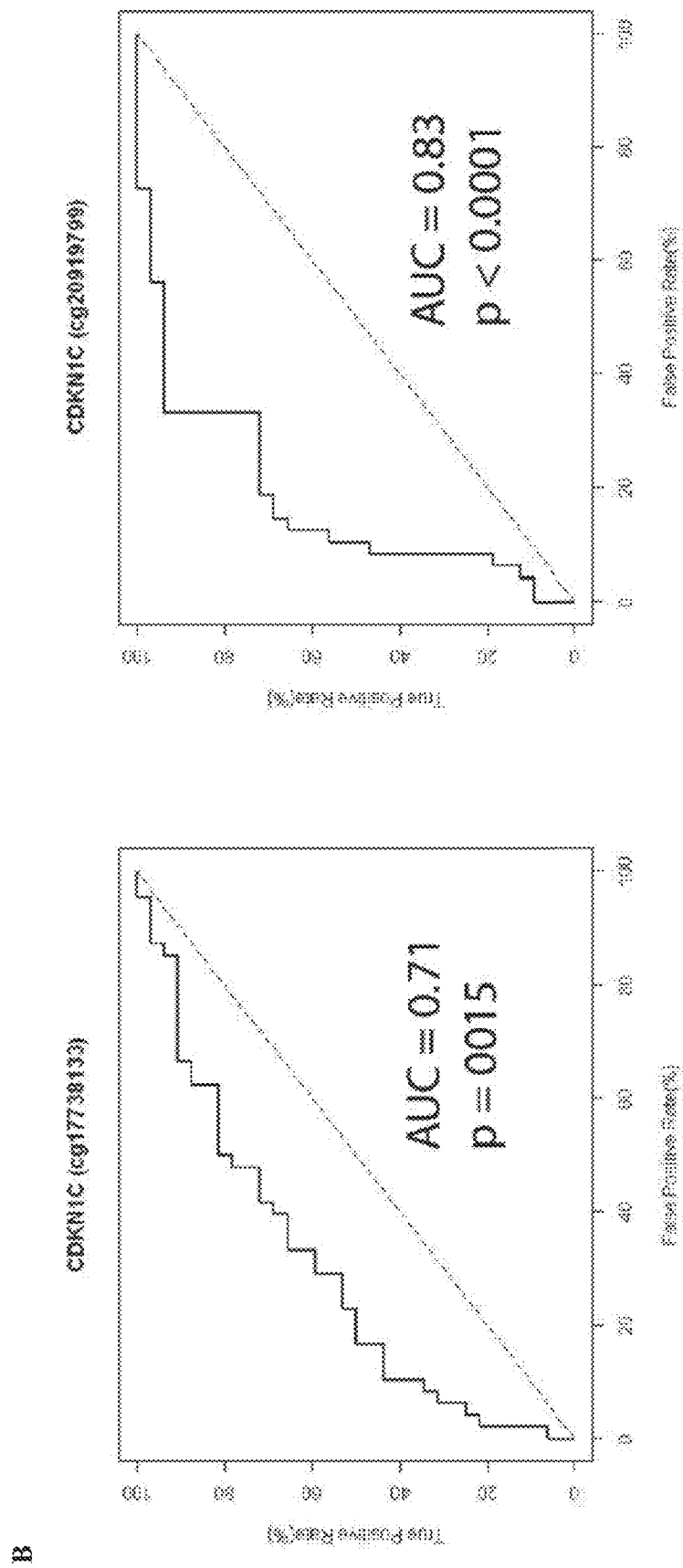
Figure 6:
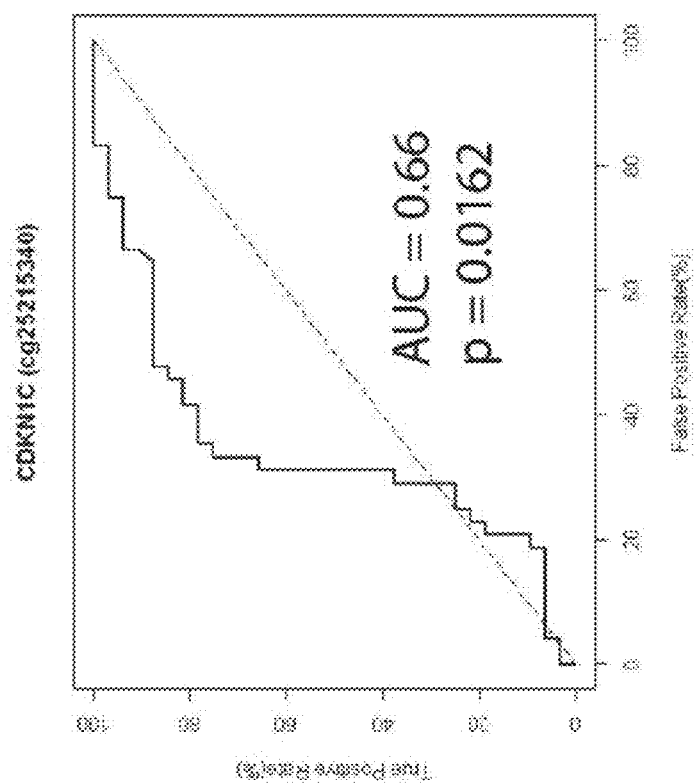
Figure 6:
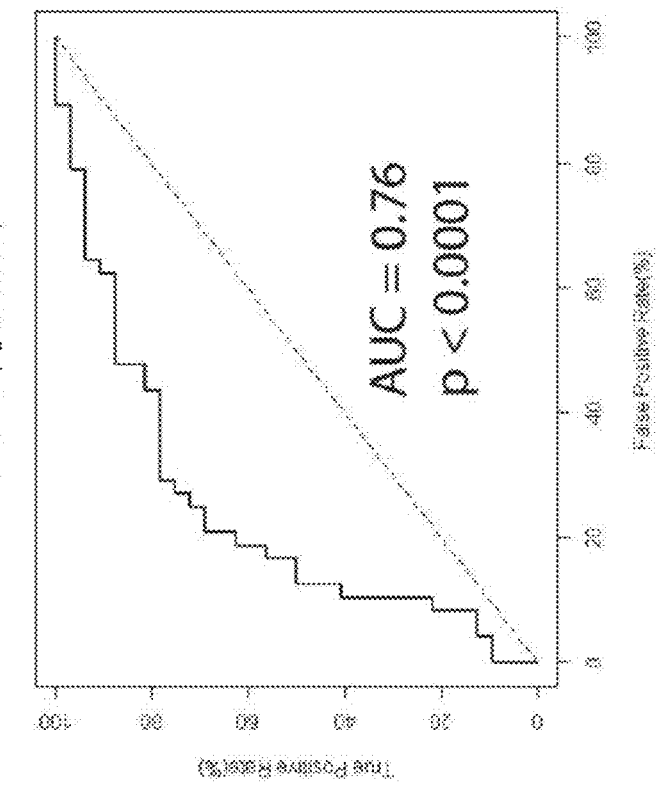

Example 7. Combined Gene Expression and DNA Methylation Analysis on Single Tumors Similarly, a combined gene expression and methylation analysis was conducted on a sample-by-sample basis for 11 samples in our cohort. Gene expression and methylation data for each sample were compared against non-neoplastic tissue. Differentially expressed genes with $\log_2$ fold-changes ≥2 or ≤2 and which had a corresponding methylation change with delta beta values >|0.2| were used for further analysis. The resultant gene lists were uploaded into IPA and the core analysis workflow was run with default parameters. Analysis of Molecular Functions demonstrated (sample number in parentheses) defects in Cellular Growth and Proliferation (7), Cellular Development (7), Cellular Movement (7) and Cell-Cell Signaling Interactions (8). Three samples had predicted decreased activity of cell movement and invasion of tumor cells. Two samples had predicted decrease in the motility of hematological cells such as leukocytes, granulocytes and one sample had predicted decreased activity in cell chemotaxis. Hypermethylated and downregulated genes most frequently contributing to cell motility and adhesion included: VAV1 (2), PENK (6), EDN3 (6), EDNRB (4), RELN (5) and ITGAM (4). Other genes affecting cell growth and proliferation which were frequently hypermethylated and downregulated included: CDKN1C (6), CDKN2B (3), CCND2 (4) and BANK1 (7). Other genes of interest include USP44 (6), and CRYAB (4), HSPB2 (1). In 8 samples, KRT8 (affecting adhesion and permeability of tight junctions) was found to be hypomethylated and upregulated. We used receiver operator characteristic (ROC) analysis to compare the methylation status of BANK1 and CDKN1C in breast brain metastasis samples to a series of 48 early stage primary breast cancer samples. The areas under the ROC curves were statistically significant for BANK1 (2/2 HumanMethylation27 array probes) and 6/8 CDKN1C methylation probes representing different CpG loci (p<0.01, Mann-Whitney U test). The data demonstrate differential methylation between primary breast tumors and brain metastases, where the metastatic samples were significantly more hypermethylated than primary tumors. The ROC curves for BANK1 and CDKN1C are shown in FIG. 6. These data highlight the importance of the epigenetic silencing of BANK1 and CDKN1C in the development of BBM.

There was also hypomethylation and upregulation of 6 X-linked MAGE genes (1 Basal sample), histone gene cluster (7), DNMT3B (4), and IL20 (5). CHODL was upregulated in basal like tumors and downregulated in Her2 and Luminal B tumors but we also noted hypermethylation and downregulation of CHODL in 4 Luminal B tumors. Similarly, TFF3 is highly expressed in Luminal B tumors and TFF1 is hypomethylated and overexpressed in 4 Luminal B tumors.

We further examined each sample for enrichment in canonical pathways and identified IL8 signaling, hepatic fibrsosis/hepatic stellate cell activation signaling and thyroid hormone metabolism signaling to be among the most frequently enriched pathways. In particular enrichment of IL8 signaling was due mainly to the hypermethylation and downregulation of several key genes such as ANGPT1, ANGPT2, KDR, ITGAM, ITGB2, PIK3CG, PIK3CD and TEK. BRAF and BCL2 were among the hypomethylated and overexpressed genes in this pathway.

Example 8. Combined Copy Number, Gene Expression and DNA Methylation Analysis on Single Tumors for the Identification of Putative Tumor Suppressor Genes and Oncogenes We next combined all three datasets to identify genes that had a 1 copy deletion, downregulation and hypermethylation in 11 individual samples; this was anticipated to be an indication of tumor suppressor function for these genes. We identified the following genes (chromosome and frequency in parenthesis): BNC1 (15q25, 2), CHODL (21q11, 2), CRYAB (11q23, 2), EDNRB (13q22, 1), FHL1 (Xq26, 1), HS3ST3A1 (17p12, 2), KL (13q13, 1), ME3 (11q14, 2), PENK (8q12, 1), PIK3CD (2), SCARA3 (8p21, 2), SCN3B (11q24, 2), SMYD4 (17p, 12, 2), SOX7 (8p23, 2).

Other candidate tumor suppressor genes included those that demonstrated homozygous deletions and loss of expression. Of 11 samples only the three basal-like samples had evidence of numerous homozygous deletions. basal-like tumor had the following homozygous deletions: Sample BBM6-CDKN2A, CDKN2B, DMD, DMRTA1, GTPBP6, PLCXD1, PPP2R3B, SPRY2; Sample BBM9-DMRT2, DMRT3, DOCK8, KANK1, ODZ1, RB1, SMARCA2, STAG2, VLDLR; Sample BBM15-ARHGAP24, FBXO11, FOXN2, GABPB1, HABP2, LHCGR, LILRB2, MSH6. One luminal tumor had a homozygous deletion of the QRFPR gene.

Similarly, we identified genes that were amplified, upregulated and hypomethylated. These include: CAPN9 (1q42, 3), CEBPG (19q13, 2), CTSE (1q32, 2), DNMT3B (20q11, 2), HIST1H2BJ (6p22, 2), HMGN1 (21q22, 2), IL20 (1q32, 2), MAT1A (10q32, 2), PSCA (8q24, 2), SRMS (20q13, 2), and TSPYL5 (8q22, 2).

The brain is a common sanctuary site of metastatic disease in patients with breast cancer and brain metastases are becoming increasingly prevalent as greater control over systemic disease is achieved. Given the poor clinical outcomes of patients with breast brain metastases, there is urgency to better understand the mechanisms underlying the pathogenesis of brain metastasis as well as to identify novel targeted therapies. Accordingly, we performed a comprehensive genomics and epigenomics analysis using microarray technology to measure alterations at the level of mRNA expression, DNA copy number and DNA methylation.

Copy number analysis identified a number of focal and broad regions of amplifications and deletions. Among the most notable regions of broad gains in our samples were 1q, 5p, 8q, 11q and 20q. Broad level deletions were identified in 8p, 17p, 21p and Xq. Previous studies have shown that ductal carcinoma in situ (DCIS) were associated with chromosomal gains in 1q, 8q and 17q [10]. Most commonly, deletions in DCIS have been shown to occur in 8p, 11q, 13q, 14q and 16q [11,12]. In invasive breast cancer, gains of 1q, 6p, 8q, 11q, 16p, 17q and 20q are most common and chromosomal losses have been identified in 1p, 8p, 11q, 16q, 18q and 22 [11,12]. These data point towards the emergence of chromosomal alterations that may be unique to breast cancer brain metastasis.

ATAD2 (8q24), and DERL1 (8q24) were among the frequently amplified and expressed genes suggesting they could play an important role in breast brain metastasis. ATAD2 may be a transcriptional coactivator of ESR1 required to induce the expression of estradiol target genes such as CCND1, MYC and E2F1 and may be required for histone hyperacetylation[14]. It has also been identified as a MYC cofactor and correlates with poor breast cancer outcomes [15]. The protein encoded by this gene contains two AAA domains and a bromodomain. AAA family proteins often perform chaperone-like functions that assist in the assembly, operation, or disassembly of protein complexes. DERL1 encodes a member of the derlin family of proteins and is thought to participate in an endoplasmic reticulum (ER)-associated degradation response and retrotranslocate misfolded/unfolded proteins into the cytosol for proteosomal degradation. Data in breast cancer cells showed that DERL1 expression is increased by ER stress while DERL1 knockdown resulted in decreased development of cancer cells [16]. The NEK2A gene on 1q32 was another frequently amplified and overexpressed gene in the samples we analyzed. The gene encodes a protein serine/threonine kinase that is involved in mitotic regulation. It has recently been described to contribute to the growth potential of DCIS and IDC and expression correlated to higher histological grade and lymph node metastasis [17].

Several samples had co-deletion and downregulation of CRYAB and HSPB2 (both on 11q23) due to deletion and/or hypermethylation. CRYAB (B crystallin) and HSPB2 are two members of the multigene small heat shock proteins (sHSPs) family that are typically coexpressed in the mammalian heart, but the biological roles remain poorly defined [18,19]. CRYAB has been implicated in stress-inducible translocation, antiapoptosis, remodeling of the cytoskeleton, cardioprotection, and inheritable cardiomyopathy in humans [19]. It has been reported that 11q22-23 is a frequent target for deletion during the development of many solid tumour types, including breast, ovary, cervix, stomach, bladder carcinomas and melanoma [20], suggesting tumor suppressor functions in solid tumors including breast brain metastases. Integrated copy number and gene expression analysis also revealed BRAF, AKT1, and IGF1R amplifications and deletion/downregulation of ATM, all of which belong to pathways that lend themselves to therapeutic targeting.

Differential expression analysis revealed significant ontologic profiles associated with G2-M checkpoint and proliferation. A central player in the G2-M cascade is FOXM1, which was overexpressed in a large percentage of breast brain metastases. FOXM1 is a transcriptional activator involved in proliferation, cell-cycle control, and mitosis, through the regulation of many genes involved in the mitotic checkpoint, such as AURKA, AURKB, PLK1, and CENPF. The FOXM1 gene was also recently highlighted as significantly deregulated in serous ovarian tumors and metastatic triple negative breast cancer [21].

Our DNA methylation analysis demonstrated an overall increase in methylation compared to non-neoplastic tissue. This is interesting since much more of the cancer genome is generally subject to lower methylation levels rather than higher levels of methylation[22]. Nevertheless, this is consistent with our findings demonstrating upregulation due to amplification and/or hypomethylation of DNMT3B and MAT1A. We did however demonstrate lower overall methylation in basal-like tumors, a finding also consistent with basal-like primary breast cancer (TCGA)[23].

Functional annotation of our epigenetically-regulated genes demonstrated a strong relationship to inflammatory and immunological responses and disorders. We identified a propensity of genes related to both tumor and immune cell migration and adhesion to be epigenetically silenced in a high percentage of samples.

Over the last decade, there has been a marked improvement in the understanding of the molecular profile of breast cancer, which has suggested that breast cancer may behave as a multiplicity of diseases [25,26,27]. Gene expression studies using DNA microarrays have identified at least four distinct subtypes of breast cancer, including Luminal A, Luminal B, HER2+/ER−, and the basal-like subtype [25,26, 27]. Recent work has shown that compared to the Luminal subtypes, Her2+/ER− and basal-like subtypes have a greater predilection for seeding the brain, a much shorter latency period for doing so and worst overall survival [5,28,29]. Applying the PAM50 classifier to our breast cancer brain metastasis series identified a relatively high number of Luminal B tumors compared to Her2+/ER− and basal-like subtypes. In certain aspects, therapies for treating breast cancer brain metastases requires consideration of the tumor intrinsic subtype status.

REFERENCES

1. Maher E A, Mietz J, Arteaga C L, DePinho R A, Mohla S (2009) Brain metastasis: opportunities in basic and translational research. Cancer Res 69: 6015-6020.
2. Tosoni A, Franceschi E, Brandes A A (2008) Chemotherapy in breast cancer patients with brain metastases: have new chemotherapic agents changed the clinical outcome? Crit Rev Oncol Hematol 68: 212-221.
3. Weil R J, Palmieri D C, Bronder J L, Stark A M, Steeg P S (2005) Breast cancer metastasis to the central nervous system. Am J Pathol 167: 913-920.
4. Gori S, Rimondini S, De Angelis V, Colozza M, Bisagni G, et al. (2007) Central nervous system metastases in HER-2 positive metastatic breast cancer patients treated with trastuzumab: incidence, survival, and risk factors. Oncologist 12: 766-773.
5. Kennecke H, Yerushalmi R, Woods R, Cheang M C, Voduc D, et al. (2010) Metastatic behavior of breast cancer subtypes. Journal of clinical oncology: official journal of the American Society of Clinical Oncology 28: 3271-3277.
6. Olshen A B, Venkatraman E S, Lucito R, Wigler M (2004) Circular binary segmentation for the analysis of array-based DNA copy number data. Biostatistics 5: 557-572.
7. Mermel C H, Schumacher S E, Hill B, Meyerson M L, Beroukhim R, et al. (2011) GISTIC2.0 facilitates sensitive and confident localization of the targets of focal somatic copy-number alteration in human cancers. Genome biology 12: R41.
8. Merico D, Isserlin R, Bader G D (2011) Visualizing gene-set enrichment results using the Cytoscape plug-in enrichment map. Methods in molecular biology 781: 257-277.
9. Chen J, Bardes E E, Aronow B J, Jegga A G (2009) ToppGene Suite for gene list enrichment analysis and candidate gene prioritization. Nucleic acids research 37: W305-311.
10. Wang C, Iakovlev V V, Wong V, Leung S, Warren K, et al. (2009) Genomic alterations in primary breast cancers compared with their sentinel and more distal lymph node metastases: an aCGH study. Genes, chromosomes & cancer 48: 1091-1101.
11. Nikolsky Y, Sviridov E, Yao J, Dosymbekov D, Ustyansky V, et al. (2008) Genome-wide functional synergy between amplified and mutated genes in human breast cancer. Cancer research 68: 9532-9540.
12. Yao J, Weremowicz S, Feng B, Gentleman R C, Marks J R, et al. (2006) Combined cDNA array comparative genomic hybridization and serial analysis of gene expression analysis of breast tumor progression. Cancer research 66: 4065-4078.
13. El Gammal A T, Bruchmann M, Zustin J, Isbarn H, Hellwinkel O J, et al. (2010) Chromosome 8p deletions and 8q gains are associated with tumor progression and poor prognosis in prostate cancer. Clinical cancer research: an official journal of the American Association for Cancer Research 16: 56-64.
14. Raeder M B, Birkeland E, Trovik J, Krakstad C, Shehata S, et al. (2013) Integrated Genomic Analysis of the 8q24 Amplification in Endometrial Cancers Identifies ATAD2 as Essential to MYC-Dependent Cancers. PLoS One 8: e54873.
15. Ciro M, Prosperini E, Quarto M, Grazini U, Walfridsson J, et al. (2009) ATAD2 is a novel cofactor for MYC, overexpressed and amplified in aggressive tumors. Cancer research 69: 8491-8498.
16. Wang J, Hua H, Ran Y, Zhang H, Liu W, et al. (2008) Derlin-1 is overexpressed in human breast carcinoma and protects cancer cells from endoplasmic reticulum stress-induced apoptosis. Breast cancer research: BCR 10: R7.
17. Wang S, Li W, Liu N, Zhang F, Liu H, et al. (2012) Nek2A contributes to tumorigenic growth and possibly functions as potential therapeutic target for human breast cancer. Journal of cellular biochemistry 113: 1904-1914.
18. Ishiwata T, Orosz A, Wang X, Mustafi S B, Pratt G W, et al. (2012) HSPB2 is dispensable for the cardiac hypertrophic response but reduces mitochondrial energetics following pressure overload in mice. PLoS One 7: e42118.
19. Benjamin I J, Guo Y, Srinivasan S, Boudina S, Taylor R P, et al. (2007) CRYAB and HSPB2 deficiency alters cardiac metabolism and paradoxically confers protection against myocardial ischemia in aging mice. American journal of physiology Heart and circulatory physiology 293: H3201-3209.
20. Baysal B E, Willett-Brozick J E, Taschner P E, Dauwerse J G, Devilee P, et al. (2001) A high-resolution integrated map spanning the SDHD gene at 11q23: a 1.1-Mb BAC contig, a partial transcript map and 15 new repeat polymorphisms in a tumour-suppressor region. European journal of human genetics: EJHG 9: 121-129.
21. Craig D W, O'Shaughnessy J A, Kiefer J A, Aldrich J, Sinari S, et al. (2013) Genome and transcriptome sequencing in prospective metastatic triple-negative breast cancer uncovers therapeutic vulnerabilities. Molecular cancer therapeutics 12: 104-116.
22. Ehrlich M (2002) DNA methylation in cancer: too much, but also too little. Oncogene 21: 5400-5413.
23. (2012) Comprehensive molecular portraits of human breast tumours. Nature 490: 61-70.
24. Hamilton A, Sibson N R (2013) Role of the systemic immune system in brain metastasis. Molecular and cellular neurosciences 53: 42-51.
25. Perou C M, Sorlie T, Eisen M B, van de Rijn M, Jeffrey S S, et al. (2000) Molecular portraits of human breast tumours. Nature 406: 747-752.
26. Perou C M, Parker J S, Prat A, Ellis M J, Bernard P S (2010) Clinical implementation of the intrinsic subtypes of breast cancer. The lancet oncology 11: 718-719; author reply 720-711.
27. Parker J S, Mullins M, Cheang M C, Leung S, Voduc D, et al. (2009) Supervised risk predictor of breast cancer based on intrinsic subtypes. Journal of clinical oncology: official journal of the American Society of Clinical Oncology 27: 1160-1167.
28. Smid M, Wang Y, Zhang Y, Sieuwerts A M, Yu J, et al. (2008) Subtypes of breast cancer show preferential site of relapse. Cancer research 68: 3108-3114.
29. Shao M M, Liu J, Vong J S, Niu Y, Germin B, et al. (2011) A subset of breast cancer predisposes to brain metastasis. Medical molecular morphology 44: 15-20.
30. Harrell J C, Prat A, Parker J S, Fan C, He X, et al. (2012) Genomic analysis identifies unique signatures predictive of brain, lung, and liver relapse. Breast cancer research and treatment 132: 523-535.
31. Weigelt B, Hu Z, He X, Livasy C, Carey L A, et al. (2005) Molecular portraits and 70-gene prognosis signature are preserved throughout the metastatic process of breast cancer. Cancer research 65: 9155-9158.
32. Salhia B, Kiefer J, Ross J T D, Metapally R, Martinez R A, et al. (2014) Integrated Genomic and Epigenomic Analysis of Breast Cancer Brain Metastasis. PLoS ONE 9(1): e85448. doi:10.1371/journal.pone.0085448

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

I claim:

1. A method for treating breast cancer central nervous system (CNS) metastasis in a subject, comprising:
   a) determining in a subject-derived brain or breast tissue, a methylation level of BANK1, wherein the subject has been diagnosed with breast cancer;
   b) comparing the subject-derived methylation level of BANK1 determined in step a) with a normal control methylation level of BANK1 obtained from non-metastasis brain or breast cells;
   c) diagnosing the subject as having breast cancer CNS metastasis by detecting an increase of the subject-derived methylation level of BANK1 as compared to the normal control methylation level of BANK1; and
   d) administering to the subject diagnosed as having breast cancer CNS metastasis, a compound selected from the group consisting of: Vidaza, decitabine, Entinostat, a PARP inhibitor, and combinations thereof.

2. The method of claim 1, wherein the subject has been diagnosed with a breast cancer molecular subtype of Luminal B.

3. The method of claim 1, wherein the methylation level is determined with bisulfite treatment of DNA, reverse phase high pressure liquid chromatography (HPLC), methylation sensitive PCR (MSP), bisulfite PCR, cloning differentially methylated sequences, Southern blot analysis, methylated CpG island amplification (MCA), differential methylation hybridization using CpG island arrays, isolation of CpG islands using a CpG binding column, DNA-methyltransferase assay, bisulfite modification, bisulfate pyrosequencing, methylation detection after restriction, methylation-sensitive restriction fingerprinting, restriction landmark genomic scanning (RLGS), or bisulfite conversion combined with bisulfite restriction analysis (COBRA).

4. The method of claim 3, wherein the methylation level is determined with bisulfite pyrosequencing.

5. The method of claim 1, wherein the normal control is non-metastasis brain cells from an early stage primary breast cancer sample.

6. The method of claim 1, wherein the gene method further comprises:
determining in a subject-derived brain or breast tissue, a methylation level of a gene from the group consisting of: EDNRB, RELN, CDKN1C, ITGAM, EDN3, and PENK.

7. The method of claim 1, wherein the PARP inhibitor is selected from the group consisting of: Iniparib, Olaparib, Rucaparib, Veliparib, CEP 9722, MK 4827, BMN-673, and 3-aminobenzamide.

8. The method of claim 1, wherein the method further comprises administering to the subject an inhibitor of a gene selected from the group consisting of: ATAD2, BRAF, DERL1, DNMTRB, NEK2A, AKT1, AURKA, AURKB, ESR2, FASN, FOXM1, TBX2, TNFRSFI2A, PSENEN, HIF1A, IGF1R, MCL1, PPFIA1, RAF1, PRL, RXRA, SRD5A2, SUMO2, TYMS, UBA1, VEGFA, WNT3A, HOXA7, HOXA9, HOXA10, HOXA11, ERBB2, NEUROD2, and WNT9A.

9. A method for treating breast cancer central nervous system (CNS) metastasis in a subject, comprising:
determining in a subject-derived brain or breast tissue an expression level of BANK1, wherein the subject has been diagnosed with breast cancer;
comparing the subject-derived expression level of BANK1 with a normal control expression level of BANK1 obtained from the non-metastasis brain or breast cells;
diagnosing the subject as having breast cancer CNS metastasis by detecting a reduction of the subject-derived expression level of BANK1 as compared to the normal control expression level; and
administering to the subject diagnosed as having breast cancer CNS metastasis, a compound selected from the group consisting of: Vidaza, decitabine, Entinostat, a PARP inhibitor, and combinations thereof.

10. A method for diagnosing and treating a subject with breast cancer central nervous system (CNS) metastasis, the method comprising the steps of:
diagnosing the subject as having breast cancer CNS metastasis by:
obtaining or having obtained a brain or breast sample from the subject; and
detecting hypermethylation and downregulation of BANK1; and
administering to the subject diagnosed as having breast cancer CNS metastasis, a compound selected from the group consisting of: Vidaza, decitabine, Entinostat, a PARP inhibitor, and combinations thereof.

11. The method of claim 10, wherein the breast cancer is Luminal B breast cancer, and the methylation level is determined with bisulfate pyrosequencing.

12. The method of claim 10, wherein the method further comprises detecting hypermethylation and downregulation of a gene selected from the group consisting of: EDNRB, RELN, CDKN1C, ITGAM, EDN3, and PENK.

13. A method for diagnosing and treating breast cancer central nervous system (CNS) metastasis, the method comprising:
diagnosing the presence of breast cancer CNS metastasis by determining a methylation level of BANK1 from a brain or breast tissue sample derived from a patient;
detecting hypermethylation of BANK1 in the brain or breast tissue sample; and
administering a treatment to the patient diagnosed as having breast cancer CNS metastasis comprising at least one of:
a) a compound selected from the group consisting of: Vidaza, decitabine, Entinostat, a PARP inhibitor, and combinations thereof;
b) surgery;
c) whole brain radiation; or
d) stereotactic radiosurgery (SRS).

14. The method of claim 13, wherein the method further comprises determining a methylation level of CDKN1C using the brain or breast tissue sample and detecting hypermethylation of CDKN1C in the brain or breast tissue sample.

15. The method of claim 13, wherein the method further comprises determining a methylation level of EDNRB using the brain or breast tissue sample and detecting hypermethylation of EDNRB in the brain or breast tissue sample.

16. The method of claim 13, wherein the method further comprises determining a methylation level of RELN using the brain or breast tissue sample and detecting hypermethylation of RELN in the brain or breast tissue sample.

17. The method of claim 13, wherein the method further comprises determining a methylation level of ITGAM using the brain or breast tissue sample and detecting hypermethylation of ITGAM in the brain or breast tissue sample.

18. The method of claim 13, wherein the method further comprises determining a methylation level of EDN3 using the brain or breast tissue sample and detecting hypermethylation of EDN3 in the brain or breast tissue sample.

19. The method of claim 13, wherein the method further comprises determining a methylation level of PENK using the brain or breast tissue sample and detecting hypermethylation of PENK in the brain or breast tissue sample.

20. The method of claim 13, wherein the treatment further comprises administering to the subject an inhibitor of a gene selected from the group consisting of: ATAD2, BRAF, DERL1, DNMTRB, NEK2A, AKT1, AURKA, AURKB, ESR2, FASN, FOXM1, TBX2, TNFRSFI2A, PSENEN, HIF1A, IGF1R, MCL1, PPFIA1, RAF1, PRL, RXRA, SRD5A2, SUMO2, TYMS, UBA1, VEGFA, WNT3A, HOXA7, HOXA9, HOXA10, HOXA11, ERBB2, NEUROD2, and WNT9A.

* * * * *

SEQUENCE LISTING

<160> NUMBER OF SEQ ID NOS: 12

<210> SEQ ID NO 1

```
<211> LENGTH: 19
<212> TYPE: DNA
<213> ORGANISM: Artificial Sequence
<220> FEATURE:
<223> OTHER INFORMATION: Primer

<400> SEQUENCE: 1
attgctgact tcggctggt                                              19

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gtccagggtg ccacacat                                               18

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
tggcgatctg cgagattt                                               18

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cctcctcagc tagcagcact                                             20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cctgcaagac caagataccg                                             20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tttcctccgc ctctcaaagt                                             20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
```

```
cttctctccg tcctcggatt ct                                              22
```

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8

```
gaaggtgatc cagactctga cctt                                            24
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9

```
ccactgaact tctgattcgc                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10

```
gcgtgctagc tggatgtctt                                                 20
```

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11

```
ctgcaccacc aactgcttag                                                 20
```

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12

```
gtcttctggg tggcagtgat                                                 20
```